United States Patent
Eriksson et al.

(10) Patent No.: US 10,336,821 B2
(45) Date of Patent: Jul. 2, 2019

(54) METHOD OF TREATING STROKE BY ADMINISTERING A COMPOUND THAT INHIBITS VEGF-B SIGNALING IN COMBINATION WITH A THROMBOLYTIC AGENT

(71) Applicants: CSL Limited, Parkville, Victoria (AU); B-Creative Sweden AB, Balsta (SE)

(72) Inventors: Ulf Eriksson, Stockholm (SE); Ingrid Nilsson, Stockholm (SE); Daniel Lawrence, Ann Arbor, MI (US); Enming Joe Su, Ann Arbor, MI (US)

(73) Assignees: CSL Limited, Parkville, Victoria (AU); B-Creative Sweden AB, Balsta (SE)

( * ) Notice: Subject to any disclaimer, the term of this patent is extended or adjusted under 35 U.S.C. 154(b) by 0 days.

(21) Appl. No.: 15/527,066

(22) PCT Filed: Nov. 17, 2015

(86) PCT No.: PCT/AU2015/050720
§ 371 (c)(1),
(2) Date: May 16, 2017

(87) PCT Pub. No.: WO2016/077878
PCT Pub. Date: May 26, 2016

(65) Prior Publication Data
US 2018/0237513 A1   Aug. 23, 2018

(30) Foreign Application Priority Data
Nov. 17, 2014 (AU) ................ 2014904606

(51) Int. Cl.
| | | |
|---|---|---|
| *A61K 38/48* | (2006.01) |
| *A61K 38/49* | (2006.01) |
| *A61P 7/04* | (2006.01) |
| *A61P 9/10* | (2006.01) |
| *A61K 45/06* | (2006.01) |
| *A61P 25/00* | (2006.01) |
| *C07K 16/22* | (2006.01) |
| *A61K 39/395* | (2006.01) |
| *C12N 15/113* | (2010.01) |
| *A61K 31/7105* | (2006.01) |
| *A61K 39/00* | (2006.01) |

(52) U.S. Cl.
CPC .......... *C07K 16/22* (2013.01); *A61K 31/7105* (2013.01); *A61K 38/482* (2013.01); *A61K 38/4886* (2013.01); *A61K 38/49* (2013.01); *A61K 39/3955* (2013.01); *A61K 45/06* (2013.01); *A61P 7/04* (2018.01); *A61P 9/10* (2018.01); *A61P 25/00* (2018.01); *C12N 15/1136* (2013.01); *C12Y 304/21068* (2013.01); *C12Y 304/21073* (2013.01); *C12Y 304/24029* (2013.01); *A61K 2039/505* (2013.01); *A61K 2039/545* (2013.01); *A61K 2039/55* (2013.01); *C07K 2317/76* (2013.01)

(58) Field of Classification Search
CPC ....... C07K 16/22; C07K 2317/76; A61P 9/10; A61P 25/00; A61P 7/04; C12N 15/1136; C12Y 304/21068; A61K 38/482; A61K 39/3955

See application file for complete search history.

(56) References Cited

FOREIGN PATENT DOCUMENTS

| WO | WO 2009/036149 A2 | 3/2009 |
| WO | 2009126698 A2 | 10/2009 |

OTHER PUBLICATIONS

International Search Report and Written Opinion dated Dec. 9, 2015 issued in PCT/AU2015/050720.
Medvedeva E. et al., "Effect of Semax and its C-terminal fragment Pro-Gly-Pro on the expression of VEGF family genes and their receptors in experimental focal ischemia of the rat brain", Journal of Molecular Neuroscience, 2013, vol. 49, pp. 328-333.
Zhang Z.G. et al., "VEGF enhances angiogenesis and promotes blood-brain barrier leakage in the ischemic brain", The Journal of Clinical Investigation, Oct. 2000, vol. 106, No. 7, pp. 829-838.
Soliman S. et al., "Candesartan induces a prolonged proangiogenic effect and augments endothelium-mediated neuroprotection after oxygen and glucose deprivation: Role of Vascular Endothelial Growth Factors A and B", Journal of Pharmacology and Clinical Experimental Therapeutics, Jun. 2014, vol. 349, pp. 444-457.
Hagberg, Carolina E., et al., "Targeting VEGF-B as a novel treatment for insulin resistance and type 2 diabetes"; 426, Nature, vol. 490, Oct. 18, 2012.
European Search Report dated Feb. 22, 2018 issued in corresponding case, EP 15861231.7.

*Primary Examiner* — Robert S Landsman
(74) *Attorney, Agent, or Firm* — Scully Scott Murphy and Presser

(57) ABSTRACT

A method of reducing an effect of stroke in a subject, the method comprising administering to the subject a compound that inhibits VEGF-B signaling.

16 Claims, 5 Drawing Sheets
Specification includes a Sequence Listing.

SEQUENCE LISTING

```
<160> NUMBER OF SEQ ID NOS: 47

<210> SEQ ID NO 1
<211> LENGTH: 207
<212> TYPE: PRT
<213> ORGANISM: Homo sapiens
<220> FEATURE:
<221> NAME/KEY: SIGNAL
<222> LOCATION: (1)..(21)
<223> OTHER INFORMATION: Signal sequence

<400> SEQUENCE: 1

Met Ser Pro Leu Leu Arg Arg Leu Leu Leu Ala Ala Leu Leu Gln Leu
1               5                   10                  15

Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
        35                  40                  45

Pro Arg Glu Val Val Val Pro Leu Thr Val Glu Leu Met Gly Thr Val
    50                  55                  60

Ala Lys Gln Leu Val Pro Ser Cys Val Thr Val Gln Arg Cys Gly Gly
65                  70                  75                  80
```

```
Cys Cys Pro Asp Asp Gly Leu Glu Cys Val Pro Thr Gly Gln His Gln
            85                  90                  95

Val Arg Met Gln Ile Leu Met Ile Arg Tyr Pro Ser Ser Gln Leu Gly
            100                 105                 110

Glu Met Ser Leu Glu Glu His Ser Gln Cys Glu Cys Arg Pro Lys Lys
            115                 120                 125

Lys Asp Ser Ala Val Lys Pro Asp Arg Ala Ala Thr Pro His His Arg
            130                 135                 140

Pro Gln Pro Arg Ser Val Pro Gly Trp Asp Ser Ala Pro Gly Ala Pro
145                 150                 155                 160

Ser Pro Ala Asp Ile Thr His Pro Thr Pro Ala Pro Gly Pro Ser Ala
            165                 170                 175

His Ala Ala Pro Ser Thr Thr Ser Ala Leu Thr Pro Gly Pro Ala Ala
            180                 185                 190

Ala Ala Ala Asp Ala Ala Ala Ser Ser Val Ala Lys Gly Gly Ala
            195                 200                 205

<210> SEQ ID NO 2
<211> LENGTH: 188
<212> TYPE: PRT
<213> ORGANISM: Homo sapiens
<220> FEATURE:
<221> NAME/KEY: SIGNAL
<222> LOCATION: (1)..(21)
<223> OTHER INFORMATION: Signal sequence

<400> SEQUENCE: 2

Met Ser Pro Leu Leu Arg Arg Leu Leu Leu Ala Ala Leu Leu Gln Leu
1               5                   10                  15

Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
            35                  40                  45

Pro Arg Glu Val Val Val Pro Leu Thr Val Glu Leu Met Gly Thr Val
50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
            85                  90                  95

Val Arg Met Gln Ile Leu Met Ile Arg Tyr Pro Ser Ser Gln Leu Gly
            100                 105                 110

Glu Met Ser Leu Glu Glu His Ser Gln Cys Glu Cys Arg Pro Lys Lys
            115                 120                 125

Lys Asp Ser Ala Val Lys Pro Asp Ser Pro Arg Pro Leu Cys Pro Arg
            130                 135                 140

Cys Thr Gln His His Gln Arg Pro Asp Pro Arg Thr Cys Arg Arg Arg
145                 150                 155                 160

Cys Arg Arg Arg Ser Phe Leu Arg Cys Gln Gly Arg Gly Leu Glu Leu
            165                 170                 175

Asn Pro Asp Thr Cys Arg Cys Arg Lys Leu Arg Arg
            180                 185

<210> SEQ ID NO 3
<211> LENGTH: 119
<212> TYPE: PRT
<213> ORGANISM: artificial
<220> FEATURE:
```

<223> OTHER INFORMATION: amino acid sequence from a VH of antibody 2H10

<400> SEQUENCE: 3

Val Gln Leu Gln Gln Pro Gly Thr Glu Leu Val Lys Pro Gly Ala Ser
1               5                   10                  15

Val Lys Leu Ser Cys Lys Ala Ser Gly Tyr Thr Phe Thr Gly Phe Trp
            20                  25                  30

Ile His Trp Val Lys Gln Arg Pro Gly Gln Gly Leu Glu Trp Ile Gly
        35                  40                  45

His Ile Asn Pro Gly Asn Gly Thr Asn Tyr Asn Glu Lys Phe Lys
    50                  55                  60

Arg Met Ala Thr Leu Thr Val Asp Lys Ser Ser Thr Ala Tyr Met
65                  70                  75                  80

Gln Leu Ser Ser Leu Thr Ser Glu Asp Ser Ala Val Tyr Tyr Cys Ala
            85                  90                  95

Arg Ser Tyr Ser Asn Tyr Val Arg Ala Met Asp Tyr Trp Gly Gln Gly
            100                 105                 110

Thr Ser Val Thr Val Ser Ser
            115

<210> SEQ ID NO 4
<211> LENGTH: 106
<212> TYPE: PRT
<213> ORGANISM: artificial
<220> FEATURE:
<223> OTHER INFORMATION: amino acid sequence from a VL of antibody 2H10

<400> SEQUENCE: 4

Ile Gln Met Thr Gln Thr Thr Ser Ser Leu Ser Ala Ser Leu Gly Asp
1               5                   10                  15

Arg Val Thr Ile Ser Cys Arg Ala Ser Gln Asp Ile Ser Asn Phe Leu
            20                  25                  30

Asn Trp Tyr Gln Gln Lys Pro Asp Gly Thr Val Lys Leu Leu Ile Tyr
        35                  40                  45

Tyr Thr Ser Thr Leu His Ser Gly Val Pro Ser Arg Phe Ser Gly Ser
    50                  55                  60

Gly Ser Gly Thr Asp Tyr Ser Leu Thr Ile Ser Asn Leu Glu Gln Glu
65                  70                  75                  80

Asp Ile Ala Thr Tyr Phe Cys Gln Gln Gly Lys Thr Leu Pro Pro Thr
            85                  90                  95

Phe Gly Gly Gly Thr Lys Leu Glu Ile Lys
            100                 105

<210> SEQ ID NO 5
<211> LENGTH: 119
<212> TYPE: PRT
<213> ORGANISM: artificial
<220> FEATURE:
<223> OTHER INFORMATION: amino acid sequence from a VH of a humanized
    form of antibody 2H10

<400> SEQUENCE: 5

Val Gln Leu Val Gln Ser Gly Ala Glu Val Lys Lys Pro Gly Ala Ser
1               5                   10                  15

Val Lys Val Ser Cys Lys Ala Ser Gly Tyr Thr Phe Thr Gly Phe Trp
            20                  25                  30

Ile His Trp Val Arg Gln Ala Pro Gly Gln Gly Leu Glu Trp Met Gly
        35                  40                  45

His Ile Asn Pro Gly Asn Gly Gly Thr Asn Tyr Asn Glu Lys Phe Lys
 50                  55                  60

Arg Arg Val Thr Met Thr Arg Asp Lys Ser Ile Ser Thr Ala Tyr Met
 65                  70                  75                  80

Glu Leu Ser Arg Leu Arg Ser Asp Asp Thr Ala Val Tyr Tyr Cys Ala
                 85                  90                  95

Arg Ser Tyr Ser Asn Tyr Val Arg Ala Met Asp Tyr Trp Gly Gln Gly
                100                 105                 110

Thr Leu Val Thr Val Ser Ser
        115

<210> SEQ ID NO 6
<211> LENGTH: 107
<212> TYPE: PRT
<213> ORGANISM: artificial
<220> FEATURE:
<223> OTHER INFORMATION: amino acid sequence of a VL of a humanized
      form of antibody 2H10

<400> SEQUENCE: 6

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Phe
                 20                  25                  30

Leu Asn Trp Tyr Gln Gln Lys Pro Gly Lys Ala Pro Lys Leu Leu Ile
             35                  40                  45

Tyr Tyr Thr Ser Thr Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Lys Thr Leu Pro Pro
                 85                  90                  95

Thr Phe Gly Gly Gly Thr Lys Val Glu Ile Lys
            100                 105

<210> SEQ ID NO 7
<211> LENGTH: 116
<212> TYPE: PRT
<213> ORGANISM: artificial
<220> FEATURE:
<223> OTHER INFORMATION: amino acid sequence from a VH of antibody 4E12

<400> SEQUENCE: 7

Val Gln Pro Gln Gln Pro Gly Ala Glu Leu Val Lys Pro Gly Ala Ser
 1               5                  10                  15

Val Lys Met Ser Cys Lys Ala Ser Gly Asp Thr Phe Thr Asn Ser Trp
                 20                  25                  30

Ile Gly Trp Val Thr Gln Arg Pro Gly Gln Gly Leu Glu Trp Ile Gly
             35                  40                  45

Asp Ile Phe Pro Gly Ser Gly His Thr Asn Tyr Asn Glu Lys Phe Lys
 50                  55                  60

Asn Arg Ala Thr Leu Thr Val Asp Thr Ser Ser Ser Thr Ala Tyr Met
 65                  70                  75                  80

Leu Leu Ser Ser Leu Thr Ser Asp Asp Ser Ala Val Tyr Tyr Cys Val
                 85                  90                  95

Ile Glu Asn Tyr Ala Trp Phe Ala Tyr Trp Gly Gln Gly Thr Leu Val
            100                 105                 110

Thr Val Ser Ala

<210> SEQ ID NO 8
<211> LENGTH: 107
<212> TYPE: PRT
<213> ORGANISM: artificial
<220> FEATURE:
<223> OTHER INFORMATION: amino acid sequence of a VL of antibody 4E12

<400> SEQUENCE: 8

Asp Ile Val Met Thr Gln Ser Gln Lys Phe Met Ser Ser Ser Val Gly
1               5                   10                  15

Asp Arg Val Ser Val Thr Cys Lys Ala Ser Gln Asn Val Asn Thr Asn
            20                  25                  30

Val Ala Trp Tyr Gln Gln Lys Gln Gly Gln Ser Pro Arg Pro Leu Ile
        35                  40                  45

Tyr Ser Ala Ser Ser Arg Cys Ser Gly Val Pro Asp Arg Phe Thr Gly
    50                  55                  60

Ser Gly Phe Gly Thr Asp Phe Thr Leu Thr Ile Ser Asn Val Gln Ser
65                  70                  75                  80

Glu Asp Leu Ala Glu Tyr Phe Cys Gln Gln Tyr His Ser Phe Pro Leu
                85                  90                  95

Thr Phe Gly Ala Gly Ala Lys Leu Asp Leu Lys
            100                 105

<210> SEQ ID NO 9
<211> LENGTH: 118
<212> TYPE: PRT
<213> ORGANISM: artificial
<220> FEATURE:
<223> OTHER INFORMATION: amino acid sequence from a VH of antibody 2F5

<400> SEQUENCE: 9

Val Gln Leu Gln Gln Ser Gly Pro Glu Leu Val Lys Pro Gly Thr Ser
1               5                   10                  15

Val Arg Ile Ser Cys Lys Ala Ser Gly Tyr Thr Phe Thr Thr Phe Tyr
            20                  25                  30

Ile His Trp Val Lys Gln Arg Pro Gly Gln Gly Leu Glu Trp Ile Gly
        35                  40                  45

Trp Phe Tyr Pro Gly Asn Val Asn Thr Asn Tyr Asn Glu Lys Leu Lys
    50                  55                  60

Gly Lys Ala Thr Leu Thr Ala Asp Lys Ser Ser Ser Ala Ala Tyr Leu
65                  70                  75                  80

Gln Leu Asn Ser Leu Thr Ser Glu Asp Ser Ala Val Tyr Phe Cys Thr
                85                  90                  95

Arg Ser Pro Tyr Tyr Gly Tyr Val Phe Asp Tyr Trp Gly Gln Gly Thr
            100                 105                 110

Thr Leu Thr Val Ser Ser
        115

<210> SEQ ID NO 10
<211> LENGTH: 107
<212> TYPE: PRT
<213> ORGANISM: artificial
<220> FEATURE:
<223> OTHER INFORMATION: amino acid sequence of a VL of antibody 2F5

<400> SEQUENCE: 10

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
                35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Leu Thr
                85                  90                  95

Phe Gly Ala Gly Ala Thr Lys Leu Glu Leu Lys
            100                 105

<210> SEQ ID NO 11
<211> LENGTH: 527
<212> TYPE: PRT
<213> ORGANISM: Artificial Sequence
<220> FEATURE:
<223> OTHER INFORMATION: Recombinant human tissue plasminogen activator

<400> SEQUENCE: 11

Ser Tyr Gln Val Ile Cys Arg Asp Glu Lys Thr Gln Met Ile Tyr Gln
1               5                   10                  15

Gln His Gln Ser Trp Leu Arg Pro Val Leu Arg Ser Asn Arg Val Glu
            20                  25                  30

Tyr Cys Trp Cys Asn Ser Gly Arg Ala Gln Cys His Ser Val Pro Val
        35                  40                  45

Lys Ser Cys Ser Glu Pro Arg Cys Phe Asn Gly Gly Thr Cys Gln Gln
    50                  55                  60

Ala Leu Tyr Phe Ser Asp Phe Val Cys Gln Cys Pro Glu Gly Phe Ala
65                  70                  75                  80

Gly Lys Cys Cys Glu Ile Asp Thr Arg Ala Thr Cys Tyr Glu Asp Gln
            85                  90                  95

Gly Ile Ser Tyr Arg Gly Thr Trp Ser Thr Ala Glu Ser Gly Ala Glu
            100                 105                 110

Cys Thr Asn Trp Asn Ser Ser Ala Leu Ala Gln Lys Pro Tyr Ser Gly
        115                 120                 125

Arg Arg Pro Asp Ala Ile Arg Leu Gly Leu Gly Asn His Asn Tyr Cys
    130                 135                 140

Arg Asn Pro Asp Arg Asp Ser Lys Pro Trp Cys Tyr Val Phe Lys Ala
145                 150                 155                 160

Gly Lys Tyr Ser Ser Glu Phe Cys Ser Thr Pro Ala Cys Ser Glu Gly
                165                 170                 175

Asn Ser Asp Cys Tyr Phe Gly Asn Gly Ser Ala Tyr Arg Gly Thr His
            180                 185                 190

Ser Leu Thr Glu Ser Gly Ala Ser Cys Leu Pro Trp Asn Ser Met Ile
        195                 200                 205

Leu Ile Gly Lys Val Tyr Thr Ala Gln Asn Pro Ser Ala Gln Ala Leu
    210                 215                 220

Gly Leu Gly Lys His Asn Tyr Cys Arg Asn Pro Asp Gly Asp Ala Lys
225                 230                 235                 240

Pro Trp Cys His Val Leu Lys Asn Arg Arg Leu Thr Trp Glu Tyr Cys
                245                 250                 255

Asp Val Pro Ser Cys Ser Thr Cys Gly Leu Arg Gln Tyr Ser Gln Pro
            260                 265                 270

```
Gln Phe Arg Ile Lys Gly Gly Leu Phe Ala Asp Ile Ala Ser His Pro
        275                 280                 285

Trp Gln Ala Ala Ile Phe Ala Lys His Arg Arg Ser Pro Gly Glu Arg
    290                 295                 300

Phe Leu Cys Gly Gly Ile Leu Ile Ser Ser Cys Trp Ile Leu Ser Ala
305                 310                 315                 320

Ala His Cys Phe Gln Glu Arg Phe Pro Pro His His Leu Thr Val Ile
                325                 330                 335

Leu Gly Arg Thr Tyr Arg Val Val Pro Gly Glu Glu Gln Lys Phe
            340                 345                 350

Glu Val Glu Lys Tyr Ile Val His Lys Glu Phe Asp Asp Thr Tyr
            355                 360                 365

Asp Asn Asp Ile Ala Leu Leu Gln Leu Lys Ser Asp Ser Ser Arg Cys
    370                 375                 380

Ala Gln Glu Ser Ser Val Val Arg Thr Val Cys Leu Pro Pro Ala Asp
385                 390                 395                 400

Leu Gln Leu Pro Asp Trp Thr Glu Cys Glu Leu Ser Gly Tyr Gly Lys
                405                 410                 415

His Glu Ala Leu Ser Pro Phe Tyr Ser Glu Arg Leu Lys Glu Ala His
            420                 425                 430

Val Arg Leu Tyr Pro Ser Ser Arg Cys Thr Ser Gln His Leu Leu Asn
    435                 440                 445

Arg Thr Val Thr Asp Asn Met Leu Cys Ala Gly Asp Thr Arg Ser Gly
    450                 455                 460

Gly Pro Gln Ala Asn Leu His Asp Ala Cys Gln Gly Asp Ser Gly Gly
465                 470                 475                 480

Pro Leu Val Cys Leu Asn Asp Gly Arg Met Thr Leu Val Gly Ile Ile
                485                 490                 495

Ser Trp Gly Leu Gly Cys Gly Gln Lys Asp Val Pro Gly Val Tyr Thr
            500                 505                 510

Lys Val Thr Asn Tyr Leu Asp Trp Ile Arg Asp Asn Met Arg Pro
    515                 520                 525

<210> SEQ ID NO 12
<211> LENGTH: 33
<212> TYPE: DNA
<213> ORGANISM: Artificial Sequence
<220> FEATURE:
<223> OTHER INFORMATION: Nucleotide sequence of 2H10 VL CDR1

<400> SEQUENCE: 12
agggcaagtc aggacattag caatttttta aac                                  33

<210> SEQ ID NO 13
<211> LENGTH: 21
<212> TYPE: DNA
<213> ORGANISM: Artificial Sequence
<220> FEATURE:
<223> OTHER INFORMATION: Nucleotide sequence of 2H10 VL CDR2

<400> SEQUENCE: 13
tacacatcaa cattacactc a                                               21

<210> SEQ ID NO 14
<211> LENGTH: 27
<212> TYPE: DNA
<213> ORGANISM: Artificial Sequence
<220> FEATURE:
```

<223> OTHER INFORMATION: Nucleotide sequence of 2H10 VL CDR3

<400> SEQUENCE: 14
caacagggta aaacgcttcc tcccacg                              27

<210> SEQ ID NO 15
<211> LENGTH: 30
<212> TYPE: DNA
<213> ORGANISM: Artificial Sequence
<220> FEATURE:
<223> OTHER INFORMATION: Nucleotide sequence of 2H10 VH CDR1

<400> SEQUENCE: 15
ggctacactt tcactggctt ctggatacac                           30

<210> SEQ ID NO 16
<211> LENGTH: 51
<212> TYPE: DNA
<213> ORGANISM: Artificial Sequence
<220> FEATURE:
<223> OTHER INFORMATION: Nucleotide sequence of 2H10 VH CDR2

<400> SEQUENCE: 16
catattaatc ctggcaatgg tggcactaac tacaatgaga agttcaagag a    51

<210> SEQ ID NO 17
<211> LENGTH: 33
<212> TYPE: DNA
<213> ORGANISM: Artificial Sequence
<220> FEATURE:
<223> OTHER INFORMATION: Nucleotide sequence of 2H10 VH CDR3

<400> SEQUENCE: 17
tcctatagta actacgtgcg ggctatggac tac                       33

<210> SEQ ID NO 18
<211> LENGTH: 11
<212> TYPE: PRT
<213> ORGANISM: Artificial Sequence
<220> FEATURE:
<223> OTHER INFORMATION: Amino acid sequence of 2H10 VL CDR1

<400> SEQUENCE: 18

Arg Ala Ser Gln Asp Ile Ser Asn Phe Leu Asn
1               5                   10

<210> SEQ ID NO 19
<211> LENGTH: 7
<212> TYPE: PRT
<213> ORGANISM: Artificial Sequence
<220> FEATURE:
<223> OTHER INFORMATION: amino acid sequence of 2H10 VL CDR2

<400> SEQUENCE: 19

Tyr Thr Ser Thr Leu His Ser
1               5

<210> SEQ ID NO 20
<211> LENGTH: 9
<212> TYPE: PRT
<213> ORGANISM: Artificial Sequence
<220> FEATURE:
<223> OTHER INFORMATION: amino acid sequence of 2H10 VL CDR3

<400> SEQUENCE: 20

Gln Gln Gly Lys Thr Leu Pro Pro Thr

```
<210> SEQ ID NO 21
<211> LENGTH: 10
<212> TYPE: PRT
<213> ORGANISM: Artificial Sequence
<220> FEATURE:
<223> OTHER INFORMATION: amino acid sequence of 2H10 VH CDR1

<400> SEQUENCE: 21

Gly Tyr Thr Phe Thr Gly Phe Trp Ile His
1               5                   10

<210> SEQ ID NO 22
<211> LENGTH: 17
<212> TYPE: PRT
<213> ORGANISM: Artificial Sequence
<220> FEATURE:
<223> OTHER INFORMATION: amino acid sequence of 2H10 VH CDR2

<400> SEQUENCE: 22

His Ile Asn Pro Gly Asn Gly Gly Thr Asn Tyr Asn Glu Lys Phe Lys
1               5                   10                  15

Arg

<210> SEQ ID NO 23
<211> LENGTH: 11
<212> TYPE: PRT
<213> ORGANISM: Artificial Sequence
<220> FEATURE:
<223> OTHER INFORMATION: amino acid sequence of 2H10 VH CDR3

<400> SEQUENCE: 23

Ser Tyr Ser Asn Tyr Val Arg Ala Met Asp Tyr
1               5                   10

<210> SEQ ID NO 24
<211> LENGTH: 33
<212> TYPE: DNA
<213> ORGANISM: Artificial Sequence
<220> FEATURE:
<223> OTHER INFORMATION: nucleotide sequence of 2F5 VL CDR1

<400> SEQUENCE: 24
aaggccagtc aggatgtggg tactgctgta gcc                              33

<210> SEQ ID NO 25
<211> LENGTH: 21
<212> TYPE: DNA
<213> ORGANISM: Artificial Sequence
<220> FEATURE:
<223> OTHER INFORMATION: nucleotide sequence of 2F5 VL CDR2

<400> SEQUENCE: 25
tgggcatcca cccggcacac t                                           21

<210> SEQ ID NO 26
<211> LENGTH: 24
<212> TYPE: DNA
<213> ORGANISM: Artificial Sequence
<220> FEATURE:
<223> OTHER INFORMATION: nucleotide sequence of 2F5 VL CDR3

<400> SEQUENCE: 26
caacaatata gcagctctct cacg                                        24
```

<210> SEQ ID NO 27
<211> LENGTH: 30
<212> TYPE: DNA
<213> ORGANISM: Artificial Sequence
<220> FEATURE:
<223> OTHER INFORMATION: nucleotide sequence of 2F5 VH CDR1

<400> SEQUENCE: 27
ggctacacct tcacaacctt ctatatacac                                    30

<210> SEQ ID NO 28
<211> LENGTH: 51
<212> TYPE: DNA
<213> ORGANISM: Artificial Sequence
<220> FEATURE:
<223> OTHER INFORMATION: nucleotide sequence of 2F5 VH CDR2

<400> SEQUENCE: 28 tggtttatc ctggaaatgt taataccaac tacaatgaga agctcaaggg c              51

<210> SEQ ID NO 29
<211> LENGTH: 30
<212> TYPE: DNA
<213> ORGANISM: Artificial Sequence
<220> FEATURE:
<223> OTHER INFORMATION: nucleotide sequence of 2F5 VH CDR3

<400> SEQUENCE: 29
tccccttact acggctacgt ttttgactac                                    30

<210> SEQ ID NO 30
<211> LENGTH: 11
<212> TYPE: PRT
<213> ORGANISM: Artificial Sequence
<220> FEATURE:
<223> OTHER INFORMATION: amino acid sequence of 2F5 VL CDR1

<400> SEQUENCE: 30

Lys Ala Ser Gln Asp Val Gly Thr Ala Val Ala
1               5                   10

<210> SEQ ID NO 31
<211> LENGTH: 7
<212> TYPE: PRT
<213> ORGANISM: Artificial Sequence
<220> FEATURE:
<223> OTHER INFORMATION: amino acid sequence of 2F5 VL CDR2

<400> SEQUENCE: 31

Trp Ala Ser Thr Arg His Thr
1               5

<210> SEQ ID NO 32
<211> LENGTH: 8
<212> TYPE: PRT
<213> ORGANISM: Artificial Sequence
<220> FEATURE:
<223> OTHER INFORMATION: amino acid sequence of 2F5 VL CDR3

<400> SEQUENCE: 32

Gln Gln Tyr Ser Ser Ser Leu Thr
1               5

<210> SEQ ID NO 33
<211> LENGTH: 10
<212> TYPE: PRT

```
<213> ORGANISM: Artificial Sequence
<220> FEATURE:
<223> OTHER INFORMATION: amino acid sequence of 2F5 VH CDR1

<400> SEQUENCE: 33

Gly Tyr Thr Phe Thr Thr Phe Tyr Ile His
1               5                   10

<210> SEQ ID NO 34
<211> LENGTH: 17
<212> TYPE: PRT
<213> ORGANISM: Artificial Sequence
<220> FEATURE:
<223> OTHER INFORMATION: amino acid sequence of 2F5 VH CDR2

<400> SEQUENCE: 34

Trp Phe Tyr Pro Gly Asn Val Asn Thr Asn Tyr Asn Glu Lys Leu Lys
1               5                   10                  15
Gly

<210> SEQ ID NO 35
<211> LENGTH: 10
<212> TYPE: PRT
<213> ORGANISM: Artificial Sequence
<220> FEATURE:
<223> OTHER INFORMATION: amino acid sequence of 2F5 VH CDR3

<400> SEQUENCE: 35

Ser Pro Tyr Tyr Gly Tyr Val Phe Asp Tyr
1               5                   10

<210> SEQ ID NO 36
<211> LENGTH: 33
<212> TYPE: DNA
<213> ORGANISM: Artificial Sequence
<220> FEATURE:
<223> OTHER INFORMATION: nucleotide sequence of 4E12 VL CDR1

<400> SEQUENCE: 36
aaggccagtc agaatgtgaa cactaatgta gcc                               33

<210> SEQ ID NO 37
<211> LENGTH: 21
<212> TYPE: DNA
<213> ORGANISM: Artificial Sequence
<220> FEATURE:
<223> OTHER INFORMATION: nucleotide sequence of 4E12 VL CDR2

<400> SEQUENCE: 37
tcggcatcct cccggtgcag t                                            21

<210> SEQ ID NO 38
<211> LENGTH: 27
<212> TYPE: DNA
<213> ORGANISM: Artificial Sequence
<220> FEATURE:
<223> OTHER INFORMATION: nucleotide sequence of 4E12 VL CDR3

<400> SEQUENCE: 38
cagcaatatc acagctttcc gctcacg                                      27

<210> SEQ ID NO 39
<211> LENGTH: 30
<212> TYPE: DNA
<213> ORGANISM: Artificial Sequence
<220> FEATURE:
```

<210> SEQ ID NO 40
<211> LENGTH: 51
<212> TYPE: DNA
<213> ORGANISM: Artificial Sequence
<220> FEATURE:
<223> OTHER INFORMATION: nucleotide sequence of 4E12 VH CDR1

<400> SEQUENCE: 39
ggcgacacct tcaccaactc ctggataggc                                      30

<210> SEQ ID NO 40
<211> LENGTH: 51
<212> TYPE: DNA
<213> ORGANISM: Artificial Sequence
<220> FEATURE:
<223> OTHER INFORMATION: nucleotide sequence of 4E12 VH CDR2

<400> SEQUENCE: 40
gatatttttc tgggagtgg tcatactaac tacaatgaga agttcaagaa c              51

<210> SEQ ID NO 41
<211> LENGTH: 24
<212> TYPE: DNA
<213> ORGANISM: Artificial Sequence
<220> FEATURE:
<223> OTHER INFORMATION: nucleotide sequence of 4E12 VH CDR3

<400> SEQUENCE: 41
gagaattatg cctggtttgc ttat                                            24

<210> SEQ ID NO 42
<211> LENGTH: 11
<212> TYPE: PRT
<213> ORGANISM: Artificial Sequence
<220> FEATURE:
<223> OTHER INFORMATION: amino acid sequence of 4E12 VL CDR1

<400> SEQUENCE: 42

Lys Ala Ser Gln Asn Val Asn Thr Asn Val Ala
1               5                   10

<210> SEQ ID NO 43
<211> LENGTH: 7
<212> TYPE: PRT
<213> ORGANISM: Artificial Sequence
<220> FEATURE:
<223> OTHER INFORMATION: amino acid sequence of 4E12 VL CDR2

<400> SEQUENCE: 43

Ser Ala Ser Ser Arg Cys Ser
1               5

<210> SEQ ID NO 44
<211> LENGTH: 9
<212> TYPE: PRT
<213> ORGANISM: Artificial Sequence
<220> FEATURE:
<223> OTHER INFORMATION: amino acid sequence of 4E12 VL CDR3

<400> SEQUENCE: 44

Gln Gln Tyr His Ser Phe Pro Leu Thr
1               5

<210> SEQ ID NO 45
<211> LENGTH: 10
<212> TYPE: PRT
<213> ORGANISM: Artificial Sequence
<220> FEATURE:
<223> OTHER INFORMATION: amino acid sequence of 4E12 VH CDR1

<400> SEQUENCE: 45

```
Gly Asp Thr Phe Thr Asn Ser Trp Ile Gly
1               5                   10

<210> SEQ ID NO 46
<211> LENGTH: 17
<212> TYPE: PRT
<213> ORGANISM: Artificial Sequence
<220> FEATURE:
<223> OTHER INFORMATION: amino acid sequence of 4E12 VH CDR2

<400> SEQUENCE: 46

Asp Ile Phe Pro Gly Ser Gly His Thr Asn Tyr Asn Glu Lys Phe Lys
1               5                   10                  15
Asn

<210> SEQ ID NO 47
<211> LENGTH: 8
<212> TYPE: PRT
<213> ORGANISM: Artificial Sequence
<220> FEATURE:
<223> OTHER INFORMATION: amino acid sequence of 4E12 VH CDR3

<400> SEQUENCE: 47

Glu Asn Tyr Ala Trp Phe Ala Tyr
1               5
```

METHOD OF TREATING STROKE BY ADMINISTERING A COMPOUND THAT INHIBITS VEGF-B SIGNALING IN COMBINATION WITH A THROMBOLYTIC AGENT

RELATED APPLICATION DATA

The present application claims priority from Australian Patent Application No. 2014904606 entitled "Method of Treating or Preventing Stroke" filed on 17 Nov. 2014. The entire contents of which are hereby incorporated by reference.

INCORPORATION BY REFERENCE OF SEQUENCE LISTING

The Sequence Listing in an ASCII text file, named 34967_Sequence_Listing.txt of 25 KB, created on May 16, 2017, and submitted to the United States Patent and Trademark Office via EFS-Web, is incorporated herein by reference.

FIELD

The present disclosure relates to methods of treating or preventing the effects of stroke in a subject by antagonizing vascular endothelial growth factor (VEGF)-B.

BACKGROUND

Stroke is the second leading cause of mortality after heart disease and the leading cause of disability in Australia. It is the third leading cause of death in the United States, with over 140,000 people dying each year from stroke. It is also the leading cause of serious, long term disability in the United States. Projected costs for stroke in USA for the period from 2005 to 2050 are US$2.2 trillion.

Disability affects 75% of stroke survivors enough to decrease their employability. Stroke can affect subjects physically, mentally, emotionally, or a combination of the three.

Some of the physical disabilities that can result from stroke include muscle weakness, numbness, pressure sores, pneumonia, incontinence, apraxia (inability to perform learned movements), difficulties carrying out daily activities, appetite loss, speech loss, vision loss, and pain. If the stroke is severe enough, or in a certain location such as parts of the brainstem, coma or death can result.

Emotional problems resulting from stroke can result from direct damage to emotional centers in the brain or from frustration and difficulty adapting to new limitations. Post-stroke emotional difficulties include depression, anxiety, panic attacks, flat affect (failure to express emotions), mania, apathy, and psychosis.

Cognitive deficits resulting from stroke include perceptual disorders, speech problems, dementia, and problems with attention and memory. A stroke sufferer may be unaware of his or her own disabilities, a condition called anosognosia. In a condition called hemispatial neglect, a patient is unable to attend to anything on the side of space opposite to the damaged hemisphere.

Up to 10% of all stroke patients develop seizures, most commonly in the week subsequent to the event. The severity of the stroke increases the likelihood of a seizure.

Stroke is the rapidly developing loss of brain function(s) due to disturbance in the blood supply to the brain. This can be due to ischemia (lack of blood flow) caused by blockage (thrombosis, arterial embolism), or a hemorrhage (leakage of blood). As a result, the affected area of the brain is unable to function, which might result in a subject's inability to move one or more limbs on one side of the body, inability to understand or formulate speech, or an inability to see one side of the visual field. Stroke often results in neuronal cell death and can lead to death.

There are two common types of stroke: (i) ischemic stroke, which is caused by a temporary or permanent occlusion to blood flow to the brain, and accounts for 85% of stroke cases, and (ii) hemorrhagic stroke, which is caused by a ruptured blood vessel and accounts for the majority of the remaining cases. The most common cause of ischemic stroke is occlusion of the middle cerebral artery (the intracranial artery downstream from the internal carotid artery), which damages cerebrum (e.g., cerebral cortex), e.g., the motor and sensory cortices of the brain. Such damage results in hemiplegia, hemi-anesthesia and, depending on the cerebral hemisphere damaged, either language or visuo-spatial deficits.

Some neuroprotective agents have been tested for efficacy in treatment of stroke, and have failed, including N-methyl-D-aspartate receptor antagonists including lubeluzole), nalmefene, clomethiazole, calcium channel blockers (including a-amino-3-hydroxy-5-rnethylisoxazole-4-propri- onic acid antagonists, serotonin agonists (e.g., repinotan), and transmembrane potassium channel modulators), tirilazad, anti-ICAM-I antibody, human antileukocytic antibody (Hu23F2G), antiplatelet antibody (e.g., abciximab), citicoline (an exogenous form of cytidine-5'-diphosphocholine), and basic fibroblast growth factor.

It will be apparent from the foregoing that there is a need in the art for therapeutics for stroke.

The growth factor VEGF-B has also been studied for an effect in neuronal survival, including after a stroke. Sun et al., *J. Cereb. Blood Flow and Metab.*, 24: 1146-1152, 2004 studied stroke in mice lacking VEGF-B and found that the lack of this growth factor resulted in significantly larger infarct volume and neurologic impairment. Li et al., *J Clin. Invest.*, 118: 913-923, 2008 showed that injection of VEGF-B into the brain of mice in which a stroke has been induced rescued neurons from apoptosis, again suggesting a role for this growth factor in providing therapeutic benefit following stroke. Extending these studies, Li et al., *Cell Adhesion and Migration*, 3: 322-327, 2009 suggested that VEGF-B protected neurons against apoptosis and mused that this growth factor may have therapeutic value in treating neurodegenerative diseases.

SUMMARY

In producing the present invention, the inventors studied the effects of inhibiting signaling of VEGF-B in an accepted mouse model of stroke, e.g., ischemic stroke. The inventors studied the effect of this growth factor by administering an antagonist of VEGF-B (e.g., an antagonistic antibody) before or after induction of stroke. Counter to what was implied by the studies discussed above, the inventors were able to reduce an effect of stroke, e.g., infarct size, intracerebral hemorrhage score or blood brain barrier breakdown. This is distinct from preventing the occurrence of a stroke. The inventors were also able to improve outcomes of thrombolytic therapy of stroke, e.g., by reducing infarct size, hemorrhages (e.g., intracerebral hemorrhages) and the number of lethal hemorrhages. The inventors also showed that administering an antagonist of VEGF-B (e.g., an antagonistic antibody) after stroke extended the time in which a thrombolytic agent could safely be administered to a subject.

The findings by the inventors provide the basis for methods for reducing the effects of stroke in a subject by inhibiting VEGF-B signaling. The findings also provide the basis for methods of prophylaxis or treatment of the effects of stroke in a subject by inhibiting VEGF-B signaling.

For example, the present disclosure provides a method of reducing an effect of stroke in a subject, the method comprising administering to the subject a compound that inhibits VEGF-B signaling.

The inventors have also found that they can reduce the incidence of hemorrhage in a subject who has suffered a stroke. Accordingly, the present disclosure additionally provides a method for reducing the incidence of hemorrhage in a subject who has suffered a stroke, the method comprising administering a compound that inhibits VEGF-B signaling. In one example, the method additionally comprises administering a thrombolytic compound.

This finding also provides the basis for methods for continuing to treat or commencing to treat a subject who has suffered a stroke to prevent a hemorrhage, e.g., an intracerebral hemorrhage, the method comprising administering a compound that inhibits VEGF-B signaling. For example, a subject can be retreated with a compound that inhibits VEGF-B signaling after a performing a method disclosed herein to reduce the risk of or to prevent a hemorrhage, e.g., an intracerebral hemorrhage.

The inventors have also found that they can reduce the likelihood of lethal hemorrhage in a subject who has suffered a stroke. Accordingly, the present disclosure additionally provides a method for reducing the likelihood of lethal hemorrhage in a subject who has suffered a stroke, the method comprising administering a compound that inhibits VEGF-B signaling. In one example, the method additionally comprises administering a thrombolytic compound.

The inventors also found that they could reduce blood-brain-barrier breakdown or leakage. Thus, the inventors have also provided a method for preventing blood-brain-barrier breakdown or leakage, the method comprising administering a compound that inhibits VEGF-B signaling. In one example, the blood-brain-barrier breakdown or leakage is associated with edema. In one example, the blood-brain-barrier breakdown or leakage is caused by an insult, e.g., trauma and/or by ischemia.

In one example of any method described herein, the compound that inhibits VEGF-B signaling is administered before or after the stroke. For example, the compound is administered prophylactically or therapeutically. In one example, the compound is administered before the stroke. In one example, the compound is administered after the stroke.

In one example of any method described herein, the compound is administered before the stroke and is administered to a subject at risk of having a stroke.

An exemplary subject at risk of having a stroke suffers from diabetes and/or obesity. For example, the diabetes is type 2 diabetes.

Additional or alternative characteristics of a subject at risk of suffering from a stroke include one or more of the following characteristics:
  has already suffered from a stroke and/or a transient ischemic attack;
  has a family history of stroke;
  suffers from heart disease;
  has high blood pressure;
  has high plasma low density lipoprotein levels;
  has metabolic syndrome has a cardiac abnormality; and/or
  has undergone surgery.

In one example, the subject is additionally aged 55 years or more, e.g., 65 years or more or 75 years or more.

In one example of any method described herein, the compound that inhibits VEGF-B signaling is administered after the stroke and the method comprises administering a combination of the compound that inhibits VEGF-B signaling and a thrombolytic compound. Accordingly, the compound that inhibits VEGF-B signaling is administered therapeutically.

In one example of any method described herein, the compound that inhibits VEGF-B signaling is administered between about 1 and 10 hours after onset of stroke symptoms. For example, the compound that inhibits VEGF-B signaling is administered between about 1 and 5 hours after onset of stroke symptoms. the compound that inhibits VEGF-B signaling is administered between about 1 and 4 hours after onset of stroke symptoms. the compound that inhibits VEGF-B signaling is administered about 1 hour after onset of stroke symptoms.

Symptoms of stroke will be apparent to the skilled person and include, for example, one or more of facial weakness, arm weakness and/or difficulty with speech. In one example of any method described herein, the compound that inhibits VEGF-B signaling is administered before the thrombolytic compound. For example, the compound that inhibits VEGF-B signaling is administered between about 1 hour and about 10 hours before the thrombolytic compound. For example, the compound that inhibits VEGF-B signaling is administered between about 1 hour and about 6 hours before the thrombolytic compound. For example, the compound that inhibits VEGF-B signaling is administered between about 2 hours and about 6 hours before the thrombolytic compound. For example, the compound that inhibits VEGF-B signaling is administered between about 3 hours and about 5 hours before the thrombolytic compound. For example, the compound that inhibits VEGF-B signaling is administered about 4 hours before the thrombolytic compound.

In one example of any method described herein, the compound that inhibits VEGF-B signaling is administered about 1 hour after onset of stroke symptoms and about 4 hours before the thrombolytic compound.

In one example of any method described herein, administration of the compound that inhibits VEGF-B signaling extends the time in which the thrombolytic compound can safely be administered to the subject. Thus, the present disclosure also provides a method for extending the time in which the thrombolytic compound can safely be administered to the subject, the method comprising administering the compound that inhibits VEGF-B signaling and then administering the thrombolytic compound.

In one example of any method described herein, the thrombolytic compound is administered more than two hours after onset of symptoms of a stroke. For example, the thrombolytic compound is administered more than three hours after onset of symptoms of a stroke. For example, the thrombolytic compound is administered more than four hours after onset of symptoms of a stroke. For example, the thrombolytic compound is administered more than five hours after onset of symptoms of a stroke.

In one example of any method described herein, the thrombolytic compound is administered between about commencement of a symptom of a stroke and about ten hours after onset of symptoms of a stroke. For example, the thrombolytic compound is administered between about four and about ten hours after onset of symptoms of a stroke. For example, the thrombolytic compound is administered between about four and about eight hours after onset of symptoms of a stroke. For example, the thrombolytic compound is administered between about three and six hours after onset of symptoms of a stroke. For example, the thrombolytic compound is administered between about four and six hours after onset of symptoms of a stroke. For example, the thrombolytic compound is administered about five hours after onset of symptoms of a stroke.

In one example of any method described herein, the compound that inhibits VEGF-B signaling is administered about 1 hour after onset of stroke symptoms and the thrombolytic compound is administered about 5 hours after onset of stroke symptoms.

In one example of any method described herein, the thrombolytic compound is selected from the group consisting of a tissue plasminogen activator, lanetoplase, reteplase, staphylokinase, streptokinase, anistreplase, desmoteplase or an urokinase.

In one example of any method described herein, the subject has elevated fasting blood glucose levels. For example, the subject has fasting blood glucose levels greater than 150 mg/dL. For example, the subject has fasting blood glucose levels greater than 180 mg/dL. For example, the subject has fasting blood glucose levels greater than 200 mg/dL. For example, the subject has fasting blood glucose levels greater than 300 mg/dL. For example, the subject has fasting blood glucose levels greater than 400 mg/dL.

In one example, the symptom of stroke is selected from:
  infarct size;
  reducing incidence of a haemorrhage in a subject;
  reducing the likelihood of lethal haemorrhage in a subject; and/or
  hemorrhage score as assessed by intracerebral hemorrhage score in the subject; and/or
  blood-brain-barrier breakdown or leakage in the subject following stroke.

In one example of any method described herein, the blood-brain-barrier breakdown or leakage in the subject following stroke may result in brain edema.

Methods for assessing each of the foregoing are known in the art and/or described herein.

Additional effects of stroke are known in the art and/or described herein and include, for example, a movement disorder such as paralysis, partial paralysis, slurred speech, uncoordinated movement, muscle weakness, hypotonicity, hypertonicity or involuntary abnormal movement.

In one example of any method described herein, the compound(s) is(are) administered in an amount sufficient to have one or more of the following effects:
  reducing infarct size in the subject;
  reducing hemorrhage score as assessed by intracerebral hemorrhage score in the subject;
  reducing blood-brain-barrier breakdown or leakage in the subject; and/or
  reducing brain edema in the subject following stroke.

In one example of any method described herein, the stroke is an ischemic stroke. For example, the stroke is a cerebral ischemic stroke.

In one example of any method described herein, a compound that inhibits VEGF-B signaling binds to VEGF-B.

For example, the compound is a protein comprising an antibody variable region that binds to or specifically binds to VEGF-B and neutralizes VEGF-B signaling.

In one example of any method described herein, the compound is an antibody mimetic. For example, the compound is a protein comprising an antigen binding domain of an immunoglobulin, e.g., an IgNAR, a camelid antibody or a T cell receptor.

In one example of any method described herein, a compound is a domain antibody (e.g., comprising only a heavy chain variable region or only a light chain variable region that binds to VEGF-B) or a heavy chain only antibody (e.g., a camelid antibody or an IgNAR) or variable region thereof.

In one example of any method described herein, a compound is a protein comprising a Fv. For example, the protein is selected from the group consisting of:
(i) a single chain Fv fragment (scFv);
(ii) a dimeric scFv (di-scFv); or
(iv) a diabody;
(v) a triabody;
(vi) a tetrabody;
(vii) a Fab;
(viii) a F(ab')$_2$;
(ix) a Fv; or
(x) one of (i) to (ix) linked to a constant region of an antibody, Fc or a heavy chain constant domain ($C_H$) 2 and/or $C_H$3.

In another example of any method described herein, a compound is an antibody. Exemplary antibodies are full-length and/or naked antibodies.

In one example of any method described herein, the compound is a protein that is recombinant, chimeric, CDR grafted, humanized, synhumanized, primatized, deimmunized or human.

In one example of any method described herein, the compound is a protein comprising an antibody variable region that competitively inhibits the binding of antibody 2H10 to VEGF-B. In one example, the protein comprises a heavy chain variable region ($V_H$) comprising a sequence set forth in SEQ ID NO: 3 and a light chain variable region ($V_L$) comprising a sequence set forth in SEQ ID NO: 4.

In one example, the compound is a protein comprising a humanized variable region of antibody 2H10. For example, the protein comprises a variable region comprising the complementarity determining regions (CDRs) of the $V_H$ and/or the $V_L$ of antibody 2H10. For example, the protein comprises:
(i) a $V_H$ comprising:
  (a) a CDR1 comprising a sequence set forth in amino acids 25-34 of SEQ ID NO: 3;
  (b) a CDR2 comprising a sequence set forth in amino acids 49-65 of SEQ ID NO: 3; and
  (c) a CDR3 comprising a sequence set forth in amino acids 98-108 of SEQ ID NO: 3; and/or
(ii) a $V_L$ comprising:
  (a) a CDR1 comprising a sequence set forth in amino acids 23-33 of SEQ ID NO: 4;
  (b) a CDR2 comprising a sequence set forth in amino acids 49-55 of SEQ ID NO: 4; and
  (c) a CDR3 comprising a sequence set forth in amino acids 88-96 of SEQ ID NO: 4.

In one example of any method described herein, the compound is a protein comprising a $V_H$ and a $V_L$, the $V_H$ and $V_L$ being humanized variable regions of antibody 2H10. For example, the protein comprises:
(i) a $V_H$ comprising:
  (a) a CDR1 comprising a sequence set forth in amino acids 25-34 of SEQ ID NO: 3;
  (b) a CDR2 comprising a sequence set forth in amino acids 49-65 of SEQ ID NO: 3; and
  (c) a CDR3 comprising a sequence set forth in amino acids 98-108 of SEQ ID NO: 3; and (ii) a $V_L$ comprising:
  (a) a CDR1 comprising a sequence set forth in amino acids 23-33 of SEQ ID NO: 4;
  (b) a CDR2 comprising a sequence set forth in amino acids 49-55 of SEQ ID NO: 4; and
  (c) a CDR3 comprising a sequence set forth in amino acids 88-96 of SEQ ID NO: 4.

As will be apparent to the skilled artisan, a sequence encoded by a nucleic acid includes all variants of that sequence that may be produced during expression.

In one example of any method described herein, the variable region or $V_H$ in any of the foregoing paragraphs comprises a sequence set forth in SEQ ID NO: 5.

In one example of any method described herein, the variable region or $V_L$ in any of the foregoing paragraphs comprises a sequence set forth in SEQ ID NO: 6.

In one example of any method described herein, the compound is an antibody.

In one example of any method described herein, the compound is an antibody comprising a $V_H$ comprising a sequence set forth in SEQ ID NO: 5 and a $V_L$ comprising a sequence set forth in SEQ ID NO: 6.

In one example, the protein or antibody is any form of the protein or antibody encoded by a nucleic acid encoding any of the foregoing proteins or antibodies.

In one example, the protein or antibody comprises:
(i) a $V_H$ comprising:
  (a) a CDR1 comprising a sequence encoded by a nucleic acid comprising SEQ ID NO: 12 or comprising an amino acid sequence of SEQ ID NO: 18;
  (b) a CDR2 comprising a sequence encoded by a nucleic acid comprising SEQ ID NO: 13 or comprising an amino acid sequence of SEQ ID NO: 19; and
  (c) a CDR3 comprising a sequence encoded by a nucleic acid comprising SEQ ID NO: 14 or comprising an amino acid sequence of SEQ ID NO: 20; and/or
(ii) a $V_L$ comprising:
  (a) a CDR1 comprising a sequence encoded by a nucleic acid comprising SEQ ID NO: 15 or comprising an amino acid sequence of SEQ ID NO: 21;
  (b) a CDR2 comprising a sequence encoded by a nucleic acid comprising SEQ ID NO: 16 or comprising an amino acid sequence of SEQ ID NO: 22; and
  (c) a CDR3 comprising a sequence encoded by a nucleic acid comprising SEQ ID NO: 17 or comprising an amino acid sequence of SEQ ID NO: 23.

In one example, the protein or antibody comprises:
(i) a $V_H$ comprising:
  (a) a CDR1 comprising a sequence encoded by a nucleic acid comprising SEQ ID NO: 24 or comprising an amino acid sequence of SEQ ID NO: 30;
  (b) a CDR2 comprising a sequence encoded by a nucleic acid comprising SEQ ID NO: 25 or comprising an amino acid sequence of SEQ ID NO: 31; and
  (c) a CDR3 comprising a sequence encoded by a nucleic acid comprising SEQ ID NO: 26 or comprising an amino acid sequence of SEQ ID NO: 32; and/or
(ii) a $V_L$ comprising:
  (a) a CDR1 comprising a sequence encoded by a nucleic acid comprising SEQ ID NO: 27 or comprising an amino acid sequence of SEQ ID NO: 33
  (b) a CDR2 comprising a sequence encoded by a nucleic acid comprising SEQ ID NO: 28 or comprising an amino acid sequence of SEQ ID NO: 34; and
  (c) a CDR3 comprising a sequence encoded by a nucleic acid comprising SEQ ID NO: 29 or comprising an amino acid sequence of SEQ ID NO: 35.

In one example, the protein or antibody comprises:
(i) a $V_H$ comprising:
  (a) a CDR1 comprising a sequence encoded by a nucleic acid comprising SEQ ID NO: 36 or comprising an amino acid sequence of SEQ ID NO: 42;
  (b) a CDR2 comprising a sequence encoded by a nucleic acid comprising SEQ ID NO: 37 or comprising an amino acid sequence of SEQ ID NO: 43; and
  (c) a CDR3 comprising a sequence encoded by a nucleic acid comprising SEQ ID NO: 38 or comprising an amino acid sequence of SEQ ID NO: 44; and/or
(ii) a $V_L$ comprising:
  (a) a CDR1 comprising a sequence encoded by a nucleic acid comprising SEQ ID NO: 39 or comprising an amino acid sequence of SEQ ID NO: 45;
  (b) a CDR2 comprising a sequence encoded by a nucleic acid comprising SEQ ID NO: 40 or comprising an amino acid sequence of SEQ ID NO: 46; and
  (c) a CDR3 comprising a sequence encoded by a nucleic acid comprising SEQ ID NO: 41 or comprising an amino acid sequence of SEQ ID NO: 47.

In one example, the compound is within a composition. For example, the composition comprises a protein comprising an antibody variable region or a $V_H$ or a $V_L$ or an antibody as described herein. In one example, the composition additionally comprises one or more variants of the protein or antibody. For example, that comprises a variant missing an encoded C-terminal lysine residue, a deamidated variant and/or a glycosylated variant and/or a variant comprising a pyroglutamate, e.g., at the N-terminus of a protein and/or a variant lacking a N-terminal residue, e.g., a N-terminal glutamine in an antibody or V region and/or a variant comprising all or part of a secretion signal. Deamidated variants of encoded asparigine residues may result in isoaspartic, and aspartic acid isoforms being generated or even a succinamide involving an adjacent amino acid residue. Deamidated variants of encoded glutamine residues may result in glutamic acid. Compositions comprising a heterogeneous mixture of such sequences and variants are intended to be included when reference is made to a particular amino acid sequence.

In one example of any method described herein, the compound that inhibits VEGF-B signaling inhibits or prevents expression of VEGF-B. For example, the compound is selected from the group an antisense, a siRNA, a RNAi, a ribozyme and a DNAzyme.

In one example of any method described herein, the VEGF-B is mammalian VEGF-B, e.g., human VEGF-B.

In one example of any method described herein, the subject is a mammal, for example a primate, such as a human.

Methods of treatment described herein can additionally comprise administering a further compound to reduce, treat or prevent the effect of a stroke.

The present disclosure also provides a compound that inhibits VEGF-B signaling for use in reducing an effect of stroke.

The present disclosure also provides for use of a compound that inhibits VEGF-B signaling in the manufacture of a medicament for reducing an effect of stroke.

The present disclosure also provides a kit comprising a compound that inhibits VEGF-B signaling packaged with instructions for use in reducing an effect of stroke. Optionally, the kit additionally comprises a thrombolytic compound.

The present disclosure also provides a kit comprising a compound that inhibits VEGF-B signaling packaged with instructions to administer the compound to a subject who has suffered a stroke in combination with a thrombolytic compound.

The present disclosure also provides a kit comprising a thrombolytic compound packaged with instructions to administer the compound to a subject who has suffered a stroke in combination with a compound that inhibits VEGF-B signaling.

Exemplary effects of stroke and compounds are described herein and are to be taken to apply mutatis mutandis to the examples of the disclosure set out in the previous six paragraphs.

KEY TO SEQUENCE LISTING

Figure 1A:
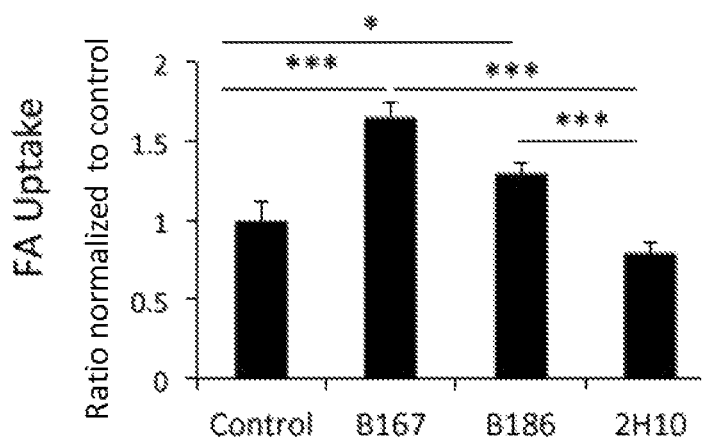
FIG. 1A is a graphical representation showing endothelial cell uptake of fatty acids is significantly increased after 2 hours treatment with VEGF-B proteins as measured using the BODIPY-C12 tracer. Values are ratio of uptake normalized to control. *P<0.05, ***P<0.001 compared to control.

SEQ ID NO: 1 is an amino acid sequence of a human VEGF-B$_{186}$ isoform containing a 21 amino acid N-terminal signal sequence SEQ ID NO: 2 is an amino acid sequence of a human VEGF-B$_{167}$ isoform containing a 21 amino acid N-terminal signal sequence SEQ ID NO: 3 is an amino acid sequence from a $V_H$ of antibody 2H10.

SEQ ID NO: 4 is an amino acid sequence from a $V_L$ of antibody 2H10.

SEQ ID NO: 5 is an amino acid sequence from a $V_H$ of a humanized form of antibody 2H10.

SEQ ID NO: 6 is an amino acid sequence of a $V_L$ of a humanized form of antibody 2H10.

SEQ ID NO: 7 is an amino acid sequence from a $V_H$ of antibody 4E12.
SEQ ID NO: 8 is an amino acid sequence of a $V_L$ of antibody 4E12.
SEQ ID NO: 9 is an amino acid sequence from a $V_H$ of antibody 2F5.
SEQ ID NO: 10 is an amino acid sequence of a $V_L$ of antibody 2F5.
SEQ ID NO: 11 is an amino acid sequence of recombinant human tissue plasminogen activator.
SEQ ID NO: 12 is a nucleotide sequence from a $V_L$ CDR1 of antibody 2H10
SEQ ID NO: 13 is a nucleotide sequence from a $V_L$ CDR2 of antibody 2H10
SEQ ID NO: 14 is a nucleotide sequence from a $V_L$ CDR3 of antibody 2H10
SEQ ID NO: 15 is a nucleotide sequence from a $V_H$ CDR1 of antibody 2H10
SEQ ID NO: 16 is a nucleotide sequence from a $V_H$ CDR2 of antibody 2H10
SEQ ID NO: 17 is a nucleotide sequence from a $V_H$ CDR3 of antibody 2H10
SEQ ID NO: 18 is an amino acid sequence from a $V_L$ CDR1 of antibody 2H10
SEQ ID NO: 19 is an amino acid sequence from a $V_L$ CDR2 of antibody 2H10
SEQ ID NO: 20 is an amino acid sequence from a $V_L$ CDR3 of antibody 2H10
SEQ ID NO: 21 is an amino acid sequence from a $V_H$ CDR1 of antibody 2H10
SEQ ID NO: 22 is an amino acid sequence from a $V_H$ CDR2 of antibody 2H10
SEQ ID NO: 23 is an amino acid sequence from a $V_H$ CDR3 of antibody 2H10
SEQ ID NO: 24 is a nucleotide sequence from a $V_L$ CDR1 of antibody 2F5
SEQ ID NO: 25 is a nucleotide sequence from a $V_L$ CDR2 of antibody 2F5
SEQ ID NO: 26 is a nucleotide sequence from a $V_L$ CDR3 of antibody 2F5
SEQ ID NO: 27 is a nucleotide sequence from a $V_H$ CDR1 of antibody 2F5
SEQ ID NO: 28 is a nucleotide sequence from a $V_H$ CDR2 of antibody 2F5
SEQ ID NO: 29 is a nucleotide sequence from a $V_H$ CDR3 of antibody 2F5
SEQ ID NO: 30 is an amino acid sequence from a $V_L$ CDR1 of antibody 2F5
SEQ ID NO: 31 is an amino acid sequence from a $V_L$ CDR2 of antibody 2F5
SEQ ID NO: 32 is an amino acid sequence from a $V_L$ CDR3 of antibody 2F5
SEQ ID NO: 33 is an amino acid sequence from a $V_H$ CDR1 of antibody 2F5
SEQ ID NO: 34 is an amino acid sequence from a $V_H$ CDR2 of antibody 2F5
SEQ ID NO: 35 is an amino acid sequence from a $V_H$ CDR3 of antibody 2F5
SEQ ID NO: 36 is a nucleotide sequence from a $V_L$ CDR1 of antibody 4E12
SEQ ID NO: 37 is a nucleotide sequence from a $V_L$ CDR2 of antibody 4E12
SEQ ID NO: 38 is a nucleotide sequence from a $V_L$ CDR3 of antibody 4E12
SEQ ID NO: 39 is a nucleotide sequence from a $V_H$ CDR1 of antibody 4E12
SEQ ID NO: 40 is a nucleotide sequence from a $V_H$ CDR2 of antibody 4E12
SEQ ID NO: 41 is a nucleotide sequence from a $V_H$ CDR3 of antibody 4E12
SEQ ID NO: 42 is an amino acid sequence from a $V_L$ CDR1 of antibody 4E12
SEQ ID NO: 43 is an amino acid sequence from a $V_L$ CDR2 of antibody 4E12
SEQ ID NO: 44 is an amino acid sequence from a $V_L$ CDR3 of antibody 4E12
SEQ ID NO: 45 is an amino acid sequence from a $V_H$ CDR1 of antibody 4E12
SEQ ID NO: 46 is an amino acid sequence from a $V_H$ CDR2 of antibody 4E12
SEQ ID NO: 47 is an amino acid sequence from a $V_H$ CDR3 of antibody 4E12

DESCRIPTION

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the present disclosure.

Any example of the present disclosure herein shall be taken to apply mutatis mutandis to any other example of the disclosure unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbor Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbor Laboratory, (1988), and J. E.

Coligan et al. (editors) Current Protocols in Immunology, John Wiley & Sons (including all updates until present).

The description and definitions of variable regions and parts thereof, immunoglobulins, antibodies and fragments thereof herein may be further clarified by the discussion in Kabat *Sequences of Proteins of Immunological Interest,* National Institutes of Health, Bethesda, Md., 1987 and 1991, Bork et al., *J Mol. Biol.* 242, 309-320, 1994, Chothia and Lesk *J. Mol Biol.* 196:901-917, 1987, Chothia et al. *Nature* 342, 877-883, 1989 and/or or Al-Lazikani et al., *J Mol Biol* 273, 927-948, 1997.

Any discussion of a protein or antibody herein will be understood to include any variants of the protein or antibody produced during manufacturing and/or storage. For example, during manufacturing or storage an antibody can be deamidated (e.g., at an asparagine or a glutamine residue) and/or have altered glycosylation and/or have a glutamine residue converted to pyroglutamate and/or have a N-terminal or C-terminal residue removed or "clipped" and/or have part or all of a signal sequence incompletely processed and, as a consequence, remain at the terminus of the antibody. It is understood that a composition comprising a particular amino acid sequence may be a heterogeneous mixture of the stated or encoded sequence and/or variants of that stated or encoded sequence.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein the term "derived from" shall be taken to indicate that a specified integer may be obtained from a particular source albeit not necessarily directly from that source.

Selected Definitions

VEGF-B is known to exist in two major isoforms, referred to as VEGF-$B_{186}$ and VEGF-$B_{167}$. For the purposes of nomenclature only and not limitation exemplary sequences of human VEGF-$B_{186}$ is set out in NCBI Reference Sequence: NP_003368.1, in NCBI protein accession numbers NP_003368, P49765 and AAL79001 and in SEQ ID NO: 1. In the context of the present disclosure, the sequence of VEGF-$B_{186}$ can lack the 21 amino acid N-terminal signal sequence (e.g., as set out at amino acids 1 to 21 of SEQ ID NO: 1. For the purposes of nomenclature only and not limitation exemplary sequences of human VEGF-$B_{167}$ is set out in NCBI Reference Sequence: NP_001230662.1, in NCBI protein accession numbers AAL79000 and AAB06274 and in SEQ ID NO: 2. In the context of the present disclosure, the sequence of VEGF-$B_{167}$ can lack the 21 amino acid N-terminal signal sequence (e.g., as set out at amino acids 1 to 21 of SEQ ID NO: 2. Additional sequence of VEGF-B can be determined using sequences provided herein and/or in publically available databases and/or determined using standard techniques (e.g., as described in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989)). Reference to human VEGF-B may be abbreviated to hVEGF-B. In one example, reference herein to VEGF-B is to VEGF-$B_{167}$ isoform.

Reference herein to VEGF-B also encompasses the VEGF-$B_{10-108}$ peptide as described in WO2006/012688.

As used herein, the term "stroke" shall be taken to mean loss of brain function(s), usually rapidly developing, that is due to a disturbance in blood flow to the brain or brainstem. The disturbance can be ischemia (lack of blood) caused by, e.g., thrombosis or embolism, or can be due to a hemorrhage. In one example, the loss of brain function is accompanied by neuronal cell death. In one example, the stroke is caused by a disturbance or loss of blood from the cerebrum or a region thereof. In one example, a stroke is a neurological deficit of cerebrovascular cause that persists beyond 24 hours or is interrupted by death within 24 hours (as defined by the World Health Organization). Persistence of symptoms beyond 24 hours separates stroke from Transient Ischemic Attack (TIA), in which symptoms persist for less than 24 hours. Symptoms of stroke include hemiplegia (paralysis of one side of the body); hemiparesis (weakness on one side of the body); muscle weakness of the face; numbness; reduction in sensation; altered sense of smell, sense of taste, hearing, or vision; loss of smell, taste, hearing, or vision; drooping of an eyelid (ptosis); detectable weakness of an ocular muscle; decreased gag reflex; decreased ability to swallow; decreased pupil reactivity to light; decreased sensation of the face; decreased balance; nystagmus; altered breathing rate; altered heart rate; weakness in sternocleidomastoid muscle with decreased ability or inability to turn the head to one side; weakness in the tongue; aphasia (inability to speak or understand language); apraxia (altered voluntary movements); a visual field defect; a memory deficit; hemineglect or hemispatial neglect (deficit in attention to the space on the side of the visual field opposite the lesion); disorganized thinking; confusion; development of hypersexual gestures; anosognosia (persistent denial of the existence of a deficit); difficulty walking; altered movement coordination; vertigo; disequilibrium; loss of consciousness; headache; and/or vomiting.

The term "effect of stroke" will be understood to include one or more of infarct size, hemorrhage score and/or blood brain barrier breakdown or leakage. However, this term is not to be limited to these effects and encompasses any change in a subject, such as any clinical change in a subject e.g., neurological or physical change, that results from a stroke. Such changes or effects include a movement disorder, loss of cerebral function or any of the symptoms described herein.

The term "onset of stroke symptoms" will be understood to refer to a time at which a subject or another person recognizes one or more symptoms of stroke. Suitable symptoms are described herein.

As used herein, the term "incidence of hemorrhage" will be understood to mean the number of or size of hemorrhages suffered by a subject or a population of subjects. Thus, a reduction in the incidence of hemorrhage in a subject can be a reduction in the number or size of hemorrhages in the subject or a reduction in the likelihood that a subject will suffer from one or more hemorrhages as a result of a stroke.

The term "likelihood of lethal hemorrhage" will be understood to mean that a subject to which the compound(s) has been administered is less likely to die as a result of a hemorrhage than a subject who has also suffered from a stroke and who has not been administered the compound(s). Clearly such likelihoods can be calculated on the basis of population data rather than requiring a side-by-side comparison for each subject. This term will also provide explicit support for reducing the likelihood of death as a result of stroke, i.e., the disclosure additionally provides methods of reducing the likelihood of death as a result of stroke. All method steps described above in relation to reducing an effect of stroke will be taken to apply equally to such methods.

The term "blood brain barrier" shall me taken to mean the highly selective permeability barrier that separates the circulating blood from the brain extra-cellular fluid in the central nervous system. Breakdown or leakage of the blood brain barrier may result in accumulation of fluid in the brain's extra-cellular space or cerebral edema. Breakdown of the blood brain barrier may result from a traumatic brain injury or from non-traumatic causes such as ischemic stroke, cancer, or brain inflammation due to meningitis or encephalitis.

The term "thrombolytic compound" shall be taken to mean a compound that induces or mediates or enhances breakdown of one or more blood clots to limit occlusion of blood vessels. The thrombolytic compound can act by stimulating secondary fibrinolysis by plasmin. Exemplary thrombolytic agents include tissue plasminogen activator (tPA), anistreplase (APSAC), streptokinase (SK), staphylokinase (SAK), desmoteplase or urokinase (uPA).

In one example, the thrombolytic compound is "tissue plasminogen activator" or tPA. tPA is a serine protease that is involved in the breakdown of blood clots by catalyzing the conversion of plasminogen to plasmin. In one example, the tissue plasminogen activator (tPA) may be manufactured using recombinant techniques. Accordingly it may be recombinant tissue plasminogen activator (r-tPA), for example comprising a sequence set forth in SEQ ID NO: 11. Exemplary tPAs include alteplase, reteplase, lanoteplase or tenecteplase.

As used herein, reference to "effective administration" (or similar) of a thrombolytic compound will mean that the administration of the thrombolytic compound provides a clinically effective outcome, i.e., an improvement in reducing the effect of a stroke compared to that seen in a subject or population of subjects in which the same thombolytic compound is administered in the same manner (e.g., at the same time and/or patients having similar blood glucose levels) with being administered an inhibitor of VEGF-B signaling.

As will be apparent to the skilled artisan based on the description herein, when discussing administering a "combination" of compounds, the present disclosure contemplates administering the compounds as a single composition, administering the compounds at the same time (but as separate compositions) or administering the compounds sequentially.

The term "recombinant" shall be understood to mean the product of artificial genetic recombination. Accordingly, in the context of a recombinant protein comprising an antibody variable region, this term does not encompass an antibody naturally-occurring within a subject's body that is the product of natural recombination that occurs during B cell maturation. However, if such an antibody is isolated, it is to be considered an isolated protein comprising an antibody variable region. Similarly, if nucleic acid encoding the protein is isolated and expressed using recombinant means, the resulting protein is a recombinant protein comprising an antibody variable region. A recombinant protein also encompasses a protein expressed by artificial recombinant means when it is within a cell, tissue or subject, e.g., in which it is expressed.

The term "protein" shall be taken to include a single polypeptide chain, i.e., a series of contiguous amino acids linked by peptide bonds or a series of polypeptide chains covalently or non-covalently linked to one another (i.e., a polypeptide complex). For example, the series of polypeptide chains can be covalently linked using a suitable chemical or a disulfide bond. Examples of non-covalent bonds include hydrogen bonds, ionic bonds, Van der Waals forces, and hydrophobic interactions.

The term "polypeptide" or "polypeptide chain" will be understood from the foregoing paragraph to mean a series of contiguous amino acids linked by peptide bonds.

The skilled artisan will be aware that an "antibody" is generally considered to be a protein that comprises a variable region made up of a plurality of polypeptide chains, e.g., a polypeptide comprising a light chain variable region ($V_L$) and a polypeptide comprising a heavy chain variable region ($V_H$). An antibody also generally comprises constant domains, some of which can be arranged into a constant region, which includes a constant fragment or fragment crystallizable (Fc), in the case of a heavy chain. A $V_H$ and a $V_L$ interact to form a Fv comprising an antigen binding region that is capable of specifically binding to one or a few closely related antigens. Generally, a light chain from mammals is either a κ light chain or a λ light chain and a heavy chain from mammals is α, δ, ε, γ, or μ. Antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass. The term "antibody" also encompasses humanized antibodies, primatized antibodies, human antibodies, synhumanized antibodies and chimeric antibodies.

The terms "full-length antibody," "intact antibody" or "whole antibody" are used interchangeably to refer to an antibody in its substantially intact form, as opposed to an antigen binding fragment of an antibody. Specifically, whole antibodies include those with heavy and light chains including an Fc region. The constant domains may be wild-type sequence constant domains (e.g., human wild-type sequence constant domains) or amino acid sequence variants thereof.

As used herein, "variable region" refers to the portions of the light and/or heavy chains of an antibody as defined herein that is capable of specifically binding to an antigen and includes amino acid sequences of complementarity determining regions (CDRs); i.e., CDR1, CDR2, and CDR3, and framework regions (FRs). Exemplary variable regions comprise three or four FRs (e.g., FR1, FR2, FR3 and optionally FR4) together with three CDRs. In the case of a protein derived from an IgNAR, the protein may lack a CDR2. $V_H$ refers to the variable region of the heavy chain. $V_L$ refers to the variable region of the light chain.

As used herein, the term "complementarity determining regions" (syn. CDRs; i.e., CDR1, CDR2, and CDR3) refers to the amino acid residues of an antibody variable domain the presence of which are necessary for antigen binding. Each variable domain typically has three CDR regions identified as CDR1, CDR2 and CDR3. The amino acid positions assigned to CDRs and FRs can be defined according to Kabat *Sequences of Proteins of Immunological Interest*, National Institutes of Health, Bethesda, Md., 1987 and 1991 or other numbering systems in the performance of this disclosure, e.g., the canonical numbering system of Chothia and Lesk *J. Mol Biol.* 196: 901-917, 1987; Chothia et al. *Nature* 342, 877-883, 1989; and/or Al-Lazikani et al., *J Mol Biol* 273: 927-948, 1997; the IMGT numbering system of Lefranc et al., *Devel. And Compar. Immunol.*, 27: 55-77, 2003; or the AHO numbering system of Honnegher and Plükthun *J. Mol. Biol.*, 309: 657-670, 2001.

"Framework regions" (FRs) are those variable domain residues other than the CDR residues.

As used herein, the term "Fv" shall be taken to mean any protein, whether comprised of multiple polypeptides or a single polypeptide, in which a $V_L$ and a $V_H$ associate and form a complex having an antigen binding site, i.e., capable of specifically binding to an antigen. The $V_H$ and the $V_L$ which form the antigen binding site can be in a single polypeptide chain or in different polypeptide chains. Furthermore, an Fv of the disclosure (as well as any protein of the disclosure) may have multiple antigen binding sites which may or may not bind the same antigen. This term shall be understood to encompass fragments directly derived from an antibody as well as proteins corresponding to such a fragment produced using recombinant means. In some examples, the $V_H$ is not linked to a heavy chain constant domain ($C_H$) 1 and/or the $V_L$ is not linked to a light chain constant domain ($C_L$). Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, e.g., $C_H2$ or $C_H3$ domain, e.g., a minibody. A "Fab fragment" consists of a monovalent antigen-binding fragment of an antibody, and can be produced by digestion of a whole antibody with the enzyme papain, to yield a fragment consisting of an intact light chain and a portion of a heavy chain or can be produced using recombinant means. A "Fab' fragment" of an antibody can be obtained by treating a whole antibody with pepsin, followed by reduction, to yield a molecule consisting of an intact light chain and a portion of a heavy chain comprising a $V_H$ and a single constant domain. Two Fab' fragments are obtained per antibody treated in this manner. A Fab' fragment can also be produced by recombinant means. A "F(ab')2 fragment" of an antibody consists of a dimer of two Fab' fragments held together by two disulfide bonds, and is obtained by treating a whole antibody molecule with the enzyme pepsin, without subsequent reduction. A "Fab$_2$" fragment is a recombinant fragment comprising two Fab fragments linked using, for example a leucine zipper or a $C_H3$ domain. A "single chain Fv" or "scFv" is a recombinant molecule containing the variable region fragment (Fv) of an antibody in which the variable region of the light chain and the variable region of the heavy chain are covalently linked by a suitable, flexible polypeptide linker.

As used herein, the term "binds" in reference to the interaction of a protein or an antigen binding site thereof with an antigen means that the interaction is dependent upon the presence of a particular structure (e.g., an antigenic determinant or epitope) on the antigen. For example, an antibody recognizes and binds to a specific protein structure rather than to proteins generally. If an antibody binds to epitope "A", the presence of a molecule containing epitope "A" (or free, unlabeled "A"), in a reaction containing labeled "A" and the protein, will reduce the amount of labeled "A" bound to the antibody.

As used herein, the term "specifically binds" or "binds specifically" shall be taken to mean that a protein of the disclosure reacts or associates more frequently, more rapidly, with greater duration and/or with greater affinity with a particular antigen or cell expressing same than it does with alternative antigens or cells. For example, a protein binds to VEGF-B with materially greater affinity (e.g., 20 fold or 40 fold or 60 fold or 80 fold to 100 fold or 150 fold or 200 fold) than it does to other growth factor (e.g., VEGF-A) or to antigens commonly recognized by polyreactive natural antibodies (i.e., by naturally occurring antibodies known to bind a variety of antigens naturally found in humans). Generally, but not necessarily, reference to binding means specific binding, and each term shall be understood to provide explicit support for the other term.

As used herein, the term "neutralize" shall be taken to mean that a protein is capable of blocking, reducing or preventing VEGF-B-signaling in a cell through the VEGF-R1. Methods for determining neutralization are known in the art and/or described herein.

As used herein, the terms "preventing", "prevent" or "prevention" include administering a compound of the disclosure to thereby stop or hinder the development of at least one symptom of a condition.

As used herein, the terms "treating", "treat" or "treatment" include administering a protein described herein to thereby reduce or eliminate at least one symptom of a specified disease or condition or to slow progression of the disease or condition.

As used herein, the term "subject" shall be taken to mean any animal including humans, for example a mammal. Exemplary subjects include but are not limited to humans and non-human primates. For example, the subject is a human.

Reducing an Effect of Stroke

The disclosure herein provides, for example, a method that reduces one or more effects of stroke in a subject comprising administering to the subject a compound that inhibits VEGF-B signaling.

In one example, the subject suffers from diabetes. For example, a subject suffering from diabetes has a clinically accepted marker of diabetes, such as:

Fasting plasma glucose of greater than or equal to 7 nmol/L or 126 mg/dl;

Casual plasma glucose (taken at any time of the day) of greater than or equal to 11.1 nmol/L or 200 mg/dl with the symptoms of diabetes.

Oral glucose tolerance test (OGTT) value of greater than or equal to 11.1 nmol/L or 200 mg/dl measured at a two-hour interval. The OGTT is given over a two or three-hour time span.

In one example, the subject suffers from type 1 diabetes.

In one example, the subject suffers from type 2 diabetes.

The methods of the present disclosure can be readily applied to any form of ischemia in the central nervous system. For example, the subject can present with sign(s) and/or symptoms of retinal ischemia. Thus, the methods of the present disclosure will be taken to apply to reducing the effect of ischemia in the central nervous system, e.g., retinal ischemia.

In one example, the subject is at risk of stroke but the onset of stoke has not yet occurred. A subject is at risk if he or she has a higher risk of developing stroke than a control population. The control population may include one or more subjects selected at random from the general population (e.g., matched by age, gender, race and/or ethnicity) who have not been diagnosed or have a family history of stroke. A subject can be considered at risk for a stroke if a "risk factor" associated with that stroke is found to be associated with that subject. A risk factor can include any activity, trait, event or property associated with a given disorder, for example, through statistical or epidemiological studies on a population of subjects. A subject can thus be classified as being at risk for a stroke even if studies identifying the underlying risk factors did not include the subject specifically. For example, a subject undergoing heart surgery is at risk of transient cerebral ischemic attack (or stroke) because the frequency of transient cerebral ischemic attack is increased in a population of subjects who have undergone heart surgery as compared to a population of subjects who have not.

In one example, a subject at risk of stroke include those undergoing a surgical procedure on the brain or central nervous system, such as endovascular surgery, clipping, stenting or microcathetherization. Such subjects also include those undergoing surgery elsewhere in the body that affects a blood vessel supplying the brain (that is connecting the brain to the heart, for example, carotid arteries and jugular veins) or on an artery supplying blood to the retina. An exemplary class of subjects are those undergoing endovascular surgery to treat a brain aneurysm. Subjects undergoing these types of surgery are at enhanced risk of stroke.

In one example subjects at risk of stroke also include patients who are smokers, hypertensive, diabetic, hypercholesterolemic. Subjects especially at a high risk are those who have had a prior stroke, minor stroke, or transient ischemic attack.

As discussed above, methods of the disclosure achieve one or more of the following effects:
  reducing infarct size in the subject;
  reducing hemorrhage score as assessed by intracerebral hemorrhage score in the subject; and/or
  reducing blood-brain-barrier breakdown or leakage in the subject; and/or
  reducing cerebral edemal in the subject following stroke.

Methods for assessing infarct size are known in the art and include, for example, echnetium-99m sestamibi single-photon emission computed tomography (SPECT), computed tomography, or magnetic resonance imaging.

Methods for assessing intracerebral hemorrhage score are described, for example, in Hemphil et al., *Stroke*, 32: 891-897, 2001. The presence of hemorrhage, e.g., intracerebral hemorrhage can be determined using, e.g., MRI or CT scanning.

Blood brain barrier breakdown/leakage/permeability can also be detected using MRI, optionally using a tracer.

In one example, a method of the disclosure reduces any symptom of stroke known in the art or described herein.

As will be apparent to the skilled person a "reduction" in a symptom or effect of stroke in a subject will be comparative to another subject who has also suffered a stroke but who has not received treatment with a method described herein. This does not necessarily require a side-by-side comparison of two subjects. Rather population data can be relied upon. For example a population of subjects suffering from stroke who have not received treatment with a method described herein (optionally, a population of similar subjects to the treated subject, e.g., age, weight, diabetic status, blood glucose levels) are assessed and the mean values are compared to results of a subject or population of subjects treated with a method described herein.

VEGF-B Signaling Inhibitors
Proteins Comprising Antibody Variable Regions

An exemplary VEGF-B signaling inhibitor comprises an antibody variable region, e.g., is an antibody or an antibody fragment that binds to VEGF-B and neutralizes VEGF-B signaling.

In one example, the antibody variable region binds specifically to VEGF-B.

Suitable antibodies and proteins comprising variable regions thereof are known in the art.

For example, anti-VEGF-B antibodies and fragments thereof are described in WO2006/012688.

In one example, the anti-VEGF-B antibody or fragment thereof is an antibody that competitively inhibits the binding of 2H10 to VEGF-B or an antigen binding fragment thereof. In one example, the anti-VEGF-B antibody or fragment thereof is antibody 2H10 or a chimeric, CDR grafted or humanized version thereof or an antigen binding fragment thereof. In this regard, antibody 2H10 comprises a $V_H$ comprising a sequence set forth in SEQ ID NO: 3 and a $V_L$ comprising a sequence set forth in SEQ ID NO: 4. Exemplary chimeric and humanized versions of this antibody are described in WO2006/012688.

In one example, the anti-VEGF-B antibody or fragment thereof comprises a $V_H$ comprising a sequence set forth in SEQ ID NO: 5 and a $V_L$ comprising a sequence set forth in SEQ ID NO: 6.

In one example, the anti-VEGF-B antibody or fragment thereof is an antibody that competitively inhibits the binding of 4E12 to VEGF-B or an antigen binding fragment thereof. In one example, the anti-VEGF-B antibody or fragment thereof is antibody 4E12 or a chimeric, CDR grafted or humanized version thereof or an antigen binding fragment thereof. In this regard, antibody 4E12 comprises a $V_H$ comprising a sequence set forth in SEQ ID NO: 7 and a $V_L$ comprising a sequence set forth in SEQ ID NO: 8.

In one example, the compound is a protein comprising a humanized variable region of antibody 4E12. For example, the protein comprises a variable region comprising the complementarity determining regions (CDRs) of the $V_H$ and/or the $V_L$ of antibody 4E12. For example, the protein comprises:
(i) a $V_H$ comprising:
  (a) a CDR1 comprising a sequence set forth in amino acids 25-34 of SEQ ID NO: 7;
  (b) a CDR2 comprising a sequence set forth in amino acids 49-65 of SEQ ID NO: 7; and
  (c) a CDR3 comprising a sequence set forth in amino acids 98-105 of SEQ ID NO: 7; and/or
(ii) a $V_L$ comprising:
  (a) a CDR1 comprising a sequence set forth in amino acids 24-34 of SEQ ID NO: 8;
  (b) a CDR2 comprising a sequence set forth in amino acids 50-56 of SEQ ID NO: 8; and
  (c) a CDR3 comprising a sequence set forth in amino acids 89-97 of SEQ ID NO: 8.

In one example, the anti-VEGF-B antibody or fragment thereof is an antibody that competitively inhibits the binding of 2F5 to VEGF-B or an antigen binding fragment thereof. In one example, the anti-VEGF-B antibody or fragment thereof is antibody 2F5 or a chimeric, CDR grafted or humanized version thereof or an antigen binding fragment thereof. In this regard, antibody 2E5 comprises a $V_H$ comprising a sequence set forth in SEQ ID NO: 9 and a $V_L$ comprising a sequence set forth in SEQ ID NO: 10.

In one example, the compound is a protein comprising a humanized variable region of antibody 2F5. For example, the protein comprises a variable region comprising the complementarity determining regions (CDRs) of the $V_H$ and/or the $V_L$ of antibody 2F5.

For example, the protein comprises:
(i) a $V_H$ comprising:
  (a) a CDR1 comprising a sequence set forth in amino acids 25-34 of SEQ ID NO: 9;
  (b) a CDR2 comprising a sequence set forth in amino acids 49-65 of SEQ ID NO: 9; and
  (c) a CDR3 comprising a sequence set forth in amino acids 98-107 of SEQ ID NO: 9; and/or
(ii) a $V_L$ comprising:
  (a) a CDR1 comprising a sequence set forth in amino acids 24-34 of SEQ ID NO: 10;

(b) a CDR2 comprising a sequence set forth in amino acids 50-56 of SEQ ID NO: 10; and
(c) a CDR3 comprising a sequence set forth in amino acids 89-96 of SEQ ID NO: 10.

In another example, an antibody or protein comprising a variable region thereof is produced using a standard method, e.g., as is known in the art or briefly described herein.

Immunization-Based Methods

To generate antibodies, VEGF-B or an epitope bearing fragment or portion thereof or a modified form thereof or nucleic acid encoding same (an "immunogen"), optionally formulated with any suitable or desired adjuvant and/or pharmaceutically acceptable carrier, is administered to a subject (for example, a non-human animal subject, such as, a mouse, a rat, a chicken etc.) in the form of an injectable composition. Exemplary non-human animals are mammals, such as murine animals (e.g., rats or mice). Injection may be intranasal, intramuscular, sub-cutaneous, intravenous, intradermal, intraperitoneal, or by other known route. Optionally, the immunogen is administered numerous times. Means for preparing and characterizing antibodies are known in the art (See, e.g., Antibodies: A Laboratory Manual, Cold Spring Harbor Laboratory, 1988). Methods for producing anti-VEGF-B antibodies in mice are described in WO2006/012688.

The production of polyclonal antibodies may be monitored by sampling blood of the immunized animal at various points following immunization. A second, booster injection, may be given, if required to achieve a desired antibody titer. The process of boosting and titering is repeated until a suitable titer is achieved. When a desired level of immunogenicity is obtained, the immunized animal is bled and the serum isolated and stored, and/or the animal is used to generate monoclonal antibodies (mAbs).

Monoclonal antibodies are exemplary antibodies contemplated by the present disclosure. Generally, production of monoclonal antibodies involves, immunizing a subject (e.g., a rodent, e.g., mouse or rat) with the immunogen under conditions sufficient to stimulate antibody producing cells. In some examples, a mouse genetically-engineered to express human antibodies and not express murine antibodies proteins, is immunized to produce an antibody (e.g., as described in PCT/US2007/008231 and/or Lonberg et al., Nature 368 (1994): 856-859). Following immunization, antibody producing somatic cells (e.g., B lymphocytes) are fused with immortal cells, e.g., immortal myeloma cells. Various methods for producing such fused cells (hybridomas) are known in the art and described, for example, in Kohler and Milstein, Nature 256, 495-497, 1975. The hybridoma cells can then be cultured under conditions sufficient for antibody production.

The present disclosure contemplates other methods for producing antibodies, e.g., ABL-MYC technology (as described, for example in Largaespada et al, Curr. Top. Microbiol. Immunol, 166, 91-96. 1990).

Library-Based Methods

The present disclosure also encompasses screening of libraries of antibodies or proteins comprising antigen binding domains thereof (e.g., comprising variable regions thereof) to identify a VEGF-B binding antibody or protein comprising a variable region thereof.

Examples of libraries contemplated by this disclosure include naïve libraries (from unchallenged subjects), immunized libraries (from subjects immunized with an antigen) or synthetic libraries. Nucleic acid encoding antibodies or regions thereof (e.g., variable regions) are cloned by conventional techniques (e.g., as disclosed in Sambrook and Russell, eds, Molecular Cloning: A Laboratory Manual, 3rd Ed, vols. 1-3, Cold Spring Harbor Laboratory Press, 2001) and used to encode and display proteins using a method known in the art. Other techniques for producing libraries of proteins are described in, for example in U.S. Pat. No. 6,300,064 (e.g., a HuCAL library of Morphosys AG); U.S. Pat. No. 5,885,793; U.S. Pat. No. 6,204,023; U.S. Pat. No. 6,291,158; or U.S. Pat. No. 6,248,516.

The proteins according to the disclosure may be soluble secreted proteins or may be presented as a fusion protein on the surface of a cell, or particle (e.g., a phage or other virus, a ribosome or a spore). Various display library formats are known in the art. For example, the library is an in vitro display library (e.g., a ribosome display library, a covalent display library or a mRNA display library, e.g., as described in U.S. Pat. No. 7,270,969). In yet another example, the display library is a phage display library wherein proteins comprising antigen binding domains of antibodies are expressed on phage, e.g., as described in U.S. Pat. No. 6,300,064; U.S. Pat. No. 5,885,793; U.S. Pat. No. 6,204,023; U.S. Pat. No. 6,291,158; or U.S. Pat. No. 6,248,516. Other phage display methods are known in the art and are contemplated by the present disclosure. Similarly, methods of cell display are contemplated by the disclosure, e.g., bacterial display libraries, e.g., as described in U.S. Pat. No. 5,516,637; yeast display libraries, e.g., as described in U.S. Pat. No. 6,423,538 or a mammalian display library.

Methods for screening display libraries are known in the art. In one example, a display library of the present disclosure is screened using affinity purification, e.g., as described in Scopes (In: Protein purification: principles and practice, Third Edition, Springer Verlag, 1994). Methods of affinity purification typically involve contacting proteins comprising antigen binding domains displayed by the library with a target antigen (e.g., VEGF-B) and, following washing, eluting those domains that remain bound to the antigen.

Any variable regions or scFvs identified by screening are readily modified into a complete antibody, if desired. Exemplary methods for modifying or reformatting variable regions or scFvs into a complete antibody are described, for example, in Jones et al., *J Immunol Methods*. 354:85-90, 2010; or Jostock et al., *J Immunol Methods*, 289: 65-80, 2004. Alternatively, or additionally, standard cloning methods are used, e.g., as described in Ausubel et al (In: Current Protocols in Molecular Biology. Wiley Interscience, ISBN 047 150338, 1987), and/or (Sambrook et al (In: Molecular Cloning: Molecular Cloning: A Laboratory Manual, Cold Spring Harbor Laboratories, New York, Third Edition 2001).

Deimmunized, Chimeric, Humanized, Synhumanized, Primatized and Human Proteins

The proteins of the present disclosure may be a humanized protein.

The term "humanized protein" shall be understood to refer to a protein comprising a human-like variable region, which includes CDRs from an antibody from a non-human species (e.g., mouse or rat or non-human primate) grafted onto or inserted into FRs from a human antibody (this type of antibody is also referred to a "CDR-grafted antibody"). Humanized proteins also include proteins in which one or more residues of the human protein are modified by one or more amino acid substitutions and/or one or more FR residues of the human protein are replaced by corresponding non-human residues. Humanized proteins may also comprise residues which are found in neither the human antibody or in the non-human antibody. Any additional regions of the protein (e.g., Fc region) are generally human. Humanization can be performed using a method known in the art, e.g., U.S. Pat. No. 5,225,539, U.S. Pat. No. 6,054,297, U.S. Pat. No. 7,566,771 or U.S. Pat. No. 5,585,089. The term "humanized protein" also encompasses a super-humanized protein, e.g., as described in U.S. Pat. No. 7,732,578.

The proteins of the present disclosure may be human proteins. The term "human protein" as used herein refers to proteins having variable and, optionally, constant antibody regions found in humans, e.g. in the human germline or somatic cells or from libraries produced using such regions. The "human" antibodies can include amino acid residues not encoded by human sequences, e.g. mutations introduced by random or site directed mutations in vitro (in particular mutations which involve conservative substitutions or mutations in a small number of residues of the protein, e.g. in 1, 2, 3, 4 or 5 of the residues of the protein). These "human antibodies" do not necessarily need to be generated as a result of an immune response of a human, rather, they can be generated using recombinant means (e.g., screening a phage display library) and/or by a transgenic animal (e.g., a mouse) comprising nucleic acid encoding human antibody constant and/or variable regions and/or using guided selection (e.g., as described in or U.S. Pat. No. 5,565,332). This term also encompasses affinity matured forms of such antibodies. For the purposes of the present disclosure, a human protein will also be considered to include a protein comprising FRs from a human antibody or FRs comprising sequences from a consensus sequence of human FRs and in which one or more of the CDRs are random or semi-random, e.g., as described in U.S. Pat. No. 6,300,064 and/or U.S. Pat. No. 6,248,516.

The proteins of the present disclosure may be synhumanized proteins. The term "synhumanized protein" refers to a protein prepared by a method described in WO2007/019620. A synhumanized protein includes a variable region of an antibody, wherein the variable region comprises FRs from a New World primate antibody variable region and CDRs from a non-New World primate antibody variable region. For example, a synhumanized protein includes a variable region of an antibody, wherein the variable region comprises FRs from a New World primate antibody variable region and CDRs from a mouse or rat antibody.

The proteins of the present disclosure may be primatized proteins. A "primatized protein" comprises variable region (s) from an antibody generated following immunization of a non-human primate (e.g., a cynomolgus macaque). Optionally, the variable regions of the non-human primate antibody are linked to human constant regions to produce a primatized antibody. Exemplary methods for producing primatized antibodies are described in U.S. Pat. No. 6,113,898.

In one example a protein of the disclosure is a chimeric protein. The term "chimeric proteins" refers to proteins in which an antigen binding domain is from a particular species (e.g., murine, such as mouse or rat) or belonging to a particular antibody class or subclass, while the remainder of the protein is from a protein derived from another species (such as, for example, human or non-human primate) or belonging to another antibody class or subclass. In one example, a chimeric protein is a chimeric antibody comprising a $V_H$ and/or a $V_L$ from a non-human antibody (e.g., a murine antibody) and the remaining regions of the antibody are from a human antibody. The production of such chimeric proteins is known in the art, and may be achieved by standard means (as described, e.g., in U.S. Pat. No. 6,331,415; U.S. Pat. No. 5,807,715; U.S. Pat. No. 4,816,567 and U.S. Pat. No. 4,816,397).

The present disclosure also contemplates a deimmunized protein, e.g., as described in WO2000/34317 and WO2004/108158. De-immunized antibodies and proteins have one or more epitopes, e.g., B cell epitopes or T cell epitopes removed (i.e., mutated) to thereby reduce the likelihood that a subject will raise an immune response against the antibody or protein.

Other Proteins Comprising Antibody Variable Regions

The present disclosure also contemplates other proteins comprising a variable region or antigen binding domain of an antibody, such as:

(i) a single-domain antibody, which is a single polypeptide chain comprising all or a portion of the $V_H$ or a $V_L$ of an antibody (see, e.g., U.S. Pat. No. 6,248,516);
(ii) diabodies, triabodies and tetrabodies, e.g., as described in U.S. Pat. No. 5,844,094 and/or US2008152586;
(iii) scFvs, e.g., as described in U.S. Pat. No. 5,260,203;
(iv) minibodies, e.g., as described in U.S. Pat. No. 5,837,821;
(v) "key and hole" bispecific proteins as described in U.S. Pat. No. 5,731,168;
(vi) heteroconjugate proteins, e.g., as described in U.S. Pat. No. 4,676,980;
(vii) heteroconjugate proteins produced using a chemical cross-linker, e.g., as described in U.S. Pat. No. 4,676,980;
(viii) Fab'-SH fragments, e.g., as described in Shalaby et al, *J. Exp. Med.*, 175: 217-225, 1992; or
(ix) $Fab_3$ (e.g., as described in EP19930302894).

Constant Domain Fusions

The present disclosure encompasses a protein comprising a variable region of an antibody and a constant region or Fc or a domain thereof, e.g., $C_H2$ and/or $C_H3$ domain. Suitable constant regions and/or domains will be apparent to the skilled artisan and/or the sequences of such polypeptides are readily available from publicly available databases. Kabat et al also provide description of some suitable constant regions/domains.

Constant regions and/or domains thereof are useful for providing biological activities such as, dimerization, extended serum half-life e.g., by binding to FcRn (neonatal Fc Receptor), antigen dependent cell cytotoxicity (ADCC), complement dependent cytotoxicity (CDC, antigen dependent cell phagocytosis (ADCP).

The present disclosure also contemplates proteins comprising mutant constant regions or domains, e.g., as described in U.S. Pat. No. 7,217,797; U.S. Pat. No. 7,217,798; or US20090041770 (having increased half-life) or US2005037000 (increased ADCC).

Stabilized Proteins

Neutralizing proteins of the present disclosure can comprise an IgG4 constant region or a stabilized IgG4 constant region. The term "stabilized IgG4 constant region" will be understood to mean an IgG4 constant region that has been modified to reduce Fab arm exchange or the propensity to undergo Fab arm exchange or formation of a half-antibody or a propensity to form a half antibody. "Fab arm exchange" refers to a type of protein modification for human IgG4, in which an IgG4 heavy chain and attached light chain (half-molecule) is swapped for a heavy-light chain pair from another IgG4 molecule. Thus, IgG4 molecules may acquire two distinct Fab arms recognizing two distinct antigens (resulting in bispecific molecules). Fab arm exchange occurs naturally in vivo and can be induced in vitro by purified blood cells or reducing agents such as reduced glutathione. A "half antibody" forms when an IgG4 antibody dissociates to form two molecules each containing a single heavy chain and a single light chain.

In one example, a stabilized IgG4 constant region comprises a proline at position 241 of the hinge region according to the system of Kabat (Kabat et al., Sequences of Proteins of Immunological Interest Washington DC United States Department of Health and Human Services, 1987 and/or 1991). This position corresponds to position 228 of the hinge region according to the EU numbering system (Kabat et al., Sequences of Proteins of Immunological Interest Washington DC United States Department of Health and Human Services, 2001 and Edelman et al., *Proc. Natl. Acad. USA*, 63, 78-85, 1969). In human IgG4, this residue is generally a serine. Following substitution of the serine for proline, the IgG4 hinge region comprises a sequence CPPC. In this regard, the skilled person will be aware that the "hinge region" is a proline-rich portion of an antibody heavy chain constant region that links the Fc and Fab regions that confers mobility on the two Fab arms of an antibody. The hinge region includes cysteine residues which are involved in inter-heavy chain disulfide bonds. It is generally defined as stretching from Glu226 to Pro243 of human IgG1 according to the numbering system of Kabat. Hinge regions of other IgG isotypes may be aligned with the IgG1 sequence by placing the first and last cysteine residues forming inter-heavy chain disulfide (S-S) bonds in the same positions (see for example WO2010/080538).

Additional Protein-Based VEGF-B Signaling Inhibitors

Other proteins that may interfere with the productive interaction of VEGF-B with its receptor include mutant VEGF-B proteins.

In one example, the inhibitor is a soluble protein comprising one or more domains of a VEGF-R1 that bind to VEGF-B (and, e.g., do not substantially bind to VEGF-A). In one example, the soluble protein additionally comprises a constant region of an antibody, such as an IgG1 antibody. For example, the soluble protein additionally comprises a Fc region and, optionally a hinge region of an antibody, e.g., an IgG1 antibody.

In one example, the protein inhibitor is an antibody mimetic, e.g., a protein scaffold comprising variable regions that bind to a target protein in a manner analogous to an antibody. A description of exemplary antibody mimetics follows.

Immunoglobulins and Immunoglobulin Fragments

An example of a compound of the present disclosure is a protein comprising a variable region of an immunoglobulin, such as a T cell receptor or a heavy chain immunoglobulin (e.g., an IgNAR, a camelid antibody).

Heavy Chain Immunoglobulins

Heavy chain immunoglobulins differ structurally from many other forms of immunoglobulin (e.g., antibodies) in so far as they comprise a heavy chain, but do not comprise a light chain. Accordingly, these immunoglobulins are also referred to as "heavy chain only antibodies". Heavy chain immunoglobulins are found in, for example, camelids and cartilaginous fish (also called IgNAR).

The variable regions present in naturally occurring heavy chain immunoglobulins are generally referred to as "$V_{HH}$ domains" in camelid Ig and V-NAR in IgNAR, in order to distinguish them from the heavy chain variable regions that are present in conventional 4-chain antibodies (which are referred to as "$V_H$ domains") and from the light chain variable regions that are present in conventional 4-chain antibodies (which are referred to as "$V_L$ domains").

Heavy chain immunoglobulins do not require the presence of light chains to bind with high affinity and with high specificity to a relevant antigen. This means that single domain binding fragments can be derived from heavy chain immunoglobulins, which are easy to express and are generally stable and soluble.

A general description of heavy chain immunoglobulins from camelids and the variable regions thereof and methods for their production and/or isolation and/or use is found inter alia in the following references WO94/04678, WO97/49805 and WO 97/49805.

A general description of heavy chain immunoglobulins from cartilaginous fish and the variable regions thereof and methods for their production and/or isolation and/or use is found inter alia in WO2005/118629.

V-Like Proteins

An example of a compound of the disclosure is a T-cell receptor. T cell receptors have two V-domains that combine into a structure similar to the Fv module of an antibody. Novotny et al., *Proc Natl Acad Sci USA* 88: 8646-8650, 1991 describes how the two V-domains of the T-cell receptor (termed alpha and beta) can be fused and expressed as a single chain polypeptide and, further, how to alter surface residues to reduce the hydrophobicity directly analogous to an antibody scFv. Other publications describing production of single-chain T-cell receptors or multimeric T cell receptors comprising two V-alpha and V-beta domains include WO1999/045110 or WO2011/107595.

Other non-antibody proteins comprising antigen binding domains include proteins with V-like domains, which are generally monomeric. Examples of proteins comprising such V-like domains include CTLA-4, CD28 and ICOS. Further disclosure of proteins comprising such V-like domains is included in WO1999/045110.

Adnectins

In one example, a compound of the disclosure is an adnectin. Adnectins are based on the tenth fibronectin type III ($^{10}$Fn3) domain of human fibronectin in which the loop regions are altered to confer antigen binding. For example, three loops at one end of the β-sandwich of the $^{10}$Fn3 domain can be engineered to enable an Adnectin to specifically recognize an antigen. For further details see US20080139791 or WO2005/056764.

Anticalins

In a further example, a compound of the disclosure is an anticalin. Anticalins are derived from lipocalins, which are a family of extracellular proteins which transport small hydrophobic molecules such as steroids, bilins, retinoids and lipids. Lipocalins have a rigid β-sheet secondary structure with a plurality of loops at the open end of the conical structure which can be engineered to bind to an antigen. Such engineered lipocalins are known as anticalins. For further description of anticalins see U.S. Pat. No. 7,250,297B1 or US20070224633.

Affibodies

In a further example, a compound of the disclosure is an affibody. An affibody is a scaffold derived from the Z domain (antigen binding domain) of Protein A of Staphylococcus aureus which can be engineered to bind to antigen. The Z domain consists of a three-helical bundle of approximately 58 amino acids. Libraries have been generated by randomization of surface residues. For further details see EP1641818.

Avimers

In a further example, a compound of the disclosure is an Avimer. Avimers are multidomain proteins derived from the A-domain scaffold family. The native domains of approximately 35 amino acids adopt a defined disulfide bonded structure. Diversity is generated by shuffling of the natural variation exhibited by the family of A-domains. For further details see WO2002088171.

DARPins

In a further example, a compound of the disclosure is a Designed Ankyrin Repeat Protein (DARPin). DARPins are derived from Ankyrin which is a family of proteins that mediate attachment of integral membrane proteins to the cytoskeleton. A single ankyrin repeat is a 33 residue motif consisting of two α-helices and a β-turn. They can be engineered to bind different target antigens by randomizing residues in the first α-helix and a β-turn of each repeat. Their binding interface can be increased by increasing the number of modules (a method of affinity maturation). For further details see US20040132028.

Methods for Producing Proteins

Recombinant Expression

In the case of a recombinant protein, nucleic acid encoding same can be cloned into expression vectors, which are then transfected into host cells, such as E. coli cells, yeast cells, insect cells, or mammalian cells, such as simian COS cells, Chinese Hamster Ovary (CHO) cells, human embryonic kidney (HEK) cells, or myeloma cells that do not otherwise produce an antibody. Exemplary cells used for expressing a protein of the disclosure are CHO cells, myeloma cells or HEK cells. Molecular cloning techniques to achieve these ends are known in the art and described, for example in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989). A wide variety of cloning and in vitro amplification methods are suitable for the construction of recombinant nucleic acids. Methods of producing recombinant antibodies are also known in the art. See U.S. Pat. No. 4,816,567 or U.S. Pat. No. 5,530,101.

Following isolation, the nucleic acid is inserted operably linked to a promoter in an expression construct or expression vector for further cloning (amplification of the DNA) or for expression in a cell-free system or in cells.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Many vectors for expression in cells are available. The vector components generally include, but are not limited to, one or more of the following: a signal sequence, a sequence encoding an antibody (e.g., derived from the information provided herein), an enhancer element, a promoter, and a transcription termination sequence. The skilled artisan will be aware of suitable sequences for expression of an antibody. Exemplary signal sequences include prokaryotic secretion signals (e.g., pelB, alkaline phosphatase, penicillinase, Ipp, or heat-stable enterotoxin II), yeast secretion signals (e.g., invertase leader, a factor leader, or acid phosphatase leader) or mammalian secretion signals (e.g., herpes simplex gD signal).

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin promoter or active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); or Chinese hamster ovary cells (CHO).

Typical promoters suitable for expression in yeast cells such as for example a yeast cell selected from the group comprising Pichia pastoris, Saccharomyces cerevisiae and S. pombe, include, but are not limited to, the ADH1 promoter, the GAL1 promoter, the GAL4 promoter, the CUP1 promoter, the PHO5 promoter, the nmt promoter, the RPR1 promoter, or the TEF1 promoter.

Means for introducing the isolated nucleic acid or expression construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, Md., USA) and/or cellfectin (Gibco, Md., USA), PEG-mediated DNA uptake, electroporation and microparticle bombardment such as by using DNA-coated tungsten or gold particles (Agracetus Inc., WI, USA) amongst others.

The host cells used to produce the antibody may be cultured in a variety of media, depending on the cell type used. Commercially available media such as Ham's F10 (Sigma), Minimal Essential Medium ((MEM), (Sigma), RPM1-1640 (Sigma), and Dulbecco's Modified Eagle's Medium ((DMEM), Sigma) are suitable for culturing mammalian cells. Media for culturing other cell types discussed herein are known in the art.

Protein Purification

Following production/expression, a protein of the disclosure is purified using a method known in the art. Such purification provides the protein of the disclosure substantially free of nonspecific protein, acids, lipids, carbohydrates, and the like. In one example, the protein will be in a preparation wherein more than about 90% (e.g. 95%, 98% or 99%) of the protein in the preparation is a protein of the disclosure.

Standard methods of peptide purification are employed to obtain an isolated protein of the disclosure, including but not limited to various high-pressure (or performance) liquid chromatography (HPLC) and non-HPLC polypeptide isolation protocols, such as size exclusion chromatography, ion exchange chromatography, hydrophobic interaction chromatography, mixed mode chromatography, phase separation methods, electrophoretic separations, precipitation methods, salting in/out methods, immunochromatography, and/or other methods.

In one example, affinity purification is useful for isolating a fusion protein comprising a label. Methods for isolating a protein using affinity chromatography are known in the art and described, for example, in Scopes (In: Protein purification: principles and practice, Third Edition, Springer Verlag, 1994). For example, an antibody or compound that binds to the label (in the case of a polyhistidine tag this may be, for example, nickel-NTA) is immobilized on a solid support. A sample comprising a protein is then contacted to the immobilized antibody or compound for a time and under conditions sufficient for binding to occur. Following washing to remove any unbound or non-specifically bound protein, the protein is eluted.

In the case of a protein comprising a Fc region of an antibody, protein A or protein G or modified forms thereof can be used for affinity purification. Protein A is useful for isolating purified proteins comprising a human γ1, γ2, or γ4 heavy chain Fc region. Protein G is recommended for all mouse Fc isotypes and for human γ3.

Nucleic Acid-Based VEGF-B Signaling Inhibitors

In one example of the disclosure, therapeutic and/or prophylactic methods as described herein according to any example of the disclosure involve reducing expression of VEGF-B. For example, such a method involves administering a compound that reduces transcription and/or translation of the nucleic acid. In one example, the compound is a nucleic acid, e.g., an antisense polynucleotide, a ribozyme, a PNA, an interfering RNA, a siRNA, a microRNA.

Antisense Nucleic Acids

The term "antisense nucleic acid" shall be taken to mean a DNA or RNA or derivative thereof (e.g., LNA or PNA), or combination thereof that is complementary to at least a portion of a specific mRNA molecule encoding a polypeptide as described herein in any example of the disclosure and capable of interfering with a post-transcriptional event such as mRNA translation. The use of antisense methods is known in the art (see for example, Hartmann and Endres (editors), Manual of Antisense Methodology, Kluwer (1999)).

An antisense nucleic acid of the disclosure will hybridize to a target nucleic acid under physiological conditions. Antisense nucleic acids include sequences that correspond to structural genes or coding regions or to sequences that effect control over gene expression or splicing. For example, the antisense nucleic acid may correspond to the targeted coding region of a nucleic acid encoding VEGF-B, or the 5'-untranslated region (UTR) or the 3'-UTR or combination of these. It may be complementary in part to intron sequences, which may be spliced out during or after transcription, for example only to exon sequences of the target gene. The length of the antisense sequence should be at least 19 contiguous nucleotides, for example, at least 50 nucleotides, such as at least 100, 200, 500 or 1000 nucleotides of a nucleic acid encoding VEGF-B. The full-length sequence complementary to the entire gene transcript may be used. The length can be 100-2000 nucleotides. The degree of identity of the antisense sequence to the targeted transcript should be at least 90%, for example, 95-100%.

Exemplary antisense nucleic acids against VEGF-B are described, for example, in WO2003/105754.

Catalytic Nucleic Acid

The term "catalytic nucleic acid" refers to a DNA molecule or DNA-containing molecule (also known in the art as a "deoxyribozyme" or "DNAzyme") or a RNA or RNA-containing molecule (also known as a "ribozyme" or "RNAzyme") which specifically recognizes a distinct substrate and catalyzes the chemical modification of this substrate. The nucleic acid bases in the catalytic nucleic acid can be bases A, C, G, T (and U for RNA).

Typically, the catalytic nucleic acid contains an antisense sequence for specific recognition of a target nucleic acid, and a nucleic acid cleaving enzymatic activity (also referred to herein as the "catalytic domain"). The types of ribozymes that are useful in this disclosure are a hammerhead ribozyme and a hairpin ribozyme.

RNA Interference

RNA interference (RNAi) is useful for specifically inhibiting the production of a particular protein. Without being limited by theory, this technology relies on the presence of dsRNA molecules that contain a sequence that is essentially identical to the mRNA of the gene of interest or part thereof, in this case an mRNA encoding a VEGF-B. Conveniently, the dsRNA can be produced from a single promoter in a recombinant vector host cell, where the sense and anti-sense sequences are flanked by an unrelated sequence which enables the sense and anti-sense sequences to hybridize to form the dsRNA molecule with the unrelated sequence forming a loop structure. The design and production of suitable dsRNA molecules for the present disclosure is well within the capacity of a person skilled in the art, particularly considering WO99/32619, WO99/53050, WO99/49029, and WO01/34815.

The length of the sense and antisense sequences that hybridize should each be at least 19 contiguous nucleotides, such as at least 30 or 50 nucleotides, for example at least 100, 200, 500 or 1000 nucleotides. The full-length sequence corresponding to the entire gene transcript may be used. The lengths can be 100-2000 nucleotides. The degree of identity of the sense and antisense sequences to the targeted transcript should be at least 85%, for example, at least 90% such as, 95-100%.

Exemplary small interfering RNA ("siRNA") molecules comprise a nucleotide sequence that is identical to about 19-21 contiguous nucleotides of the target mRNA. For example, the siRNA sequence commences with the dinucleotide AA, comprises a GC-content of about 30-70% (for example, 30-60%, such as 40-60% for example about 45%-55%), and does not have a high percentage identity to any nucleotide sequence other than the target in the genome of the mammal in which it is to be introduced, for example as determined by standard BLAST search. Exemplary siRNA that reduce expression of VEGF-B are commercially available from Santa Cruz Biotechnology or Novus Biologicals.

Short hairpin RNA (shRNA) that reduce expression of VEGF-B are also known in the art and commercially available from Santa Cruz Biotechnology.

Screening Assays

Compounds that inhibit VEGF-B signaling can be identified using techniques known in the art, e.g., as described below. Similarly, amounts of VEGF-B signaling inhibitors suitable for use in a method described herein can be determined or estimated using techniques known in the art, e.g., as described below.

Neutralization Assays

For compounds that bind to VEGF-B and inhibit signaling, a neutralization assay can be used.

In one example, a neutralization assay involves contacting VEGF-B with a compound in the presence or absence of detectably labeled soluble VEGF-R1 or contacting detectably labeled VEGF-B with a compound in the presence or absence of a cell expressing VEGF-R1 or a soluble VEGF-R1. The level of VEGF-B bound to the VEGF-R1 is then assessed. A reduced level of bound VEGF-B in the presence of the compound compared to in the absence of the compound indicates the compound inhibits VEGF-B binding to VEGF-R1 and, as a consequence VEGF-B signaling.

Another neutralization assay is described in WO2006/012688 and involves contacting a fragment of VEGF-R1 comprising the second Ig-like domain immobilized on a solid support with a subsaturating concentration of recombinant VEGF-B pre-incubated with a compound. Following washing to remove unbound protein, the immobilized protein is contacted with anti-VEGF-B antibody and the amount of bound antibody (indicative of immobilized VEGF-B) determined. A compound that reduces the level of bound antibody compared to the level in the absence of the compound is considered an inhibitor of VEGF-B signaling.

In another example, a compound that inhibits VEGF-B signaling is identified using a cell dependent on VEGF-B signaling for proliferation, e.g., a BaF3 cell modified as described in WO2006/012688 to express a chimeric receptor incorporating the intracellular domain of the human erythropoietin receptor and the extracellular domain of VEGF-R1. Cells are cultured in the presence of VEGF-B and in the presence or absence of a compound. Cell proliferation is then assessed using standard methods, e.g., colony formation assays, thymidine incorporation or uptake of another suitable marker of cell proliferation (e.g., a MTS dye reduction assay). A compound that reduces the level of proliferation in the presence of VEGF-B is considered an inhibitor of VEGF-B signaling.

Compounds can also be assessed for their ability to bind to VEGF-B using standard methods. Methods for assessing binding to a protein are known in the art, e.g., as described in Scopes (In: Protein purification: principles and practice, Third Edition, Springer Verlag, 1994). Such a method generally involves labeling the compound and contacting it with immobilized VEGF-B. Following washing to remove non-specific bound compound, the amount of label and, as a consequence, bound compound is detected. Of course, the compound can be immobilized and the VEGF-B labeled. Panning-type assays can also be used. Alternatively, or additionally, surface plasmon resonance assays can be used.

Expression Assays

A compound that reduces or prevents expression of VEGF-B is identified by contacting a cell with the compound and determining the level of expression of the VEGF-B. Suitable methods for determining gene expression at the nucleic acid level are known in the art and include, for example, quantitative polymerase chain reaction (qPCR) or microarray assays. Suitable methods for determining expression at the protein level are also known in the art and include, for example, enzyme-linked immunosorbent assay (ELISA), fluorescence linked immunosorbent assay (FLISA), immunofluorescence or Western blotting.

In Vivo Assays

Compounds described herein can be tested for activity in animal models. In one example, the animal model is a model of metabolic dysfunction and hyperglycemia. For example, the diet-induced obese (DIO) mouse model. This is a well-established experimental paradigm and mice develop excess or ectopic lipid deposition in peripheral tissues which is associated with impaired insulin sensitivity and glucose uptake and the mice exhibit obesity, hyperinsulinemia, hyperglycemia, dyslipidemia and hypertension (Harberg, C. E., et al. *Nature* 490, 426-430; Collins, S., et al. *Pysiology & Behaviour* 81, 243-248).

There are various known techniques for inducing an ischemic stroke in a non-human animal subject, such as, aorta/vena cava occlusion, external neck torniquet or cuff, hemorrhage or hypotension, intracranial hypertension or common carotid artery occlusion, two-vessel occlusion and hypotension, four-vessel occlusion, unilateral common carotid artery occlusion (in some species only), endothelin-1-induced constriction of arteries and veins, middle cerebral artery occlusion (MCAO), spontaneous brain infarction (in spontaneously hypertensive rats), macrosphere embolization, blood clot embolization or microsphere embolization. Hemorrhagic stroke can be modeled by infusion of collagenase into the brain.

In one example, the model of stroke comprises middle cerebral artery occlusion (MCAO) to produce an ischemic stroke as previously described in Su et al *Nature Medicine*, 2008; 14: 731-737.

Pharmaceutical Compositions and Methods of Treatment

A compound that inhibits VEGF-B signaling (syn. active ingredient) is useful for parenteral, topical, oral, or local administration, aerosol administration, or transdermal administration, for prophylactic or for therapeutic treatment. In one example, the compound is administered parenterally, such as subcutaneously or intravenously.

Formulation of a compound to be administered will vary according to the route of administration and formulation (e.g., solution, emulsion, capsule) selected. An appropriate pharmaceutical composition comprising compound to be administered can be prepared in a physiologically acceptable carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. A variety of appropriate aqueous carriers are known to the skilled artisan, including water, buffered water, buffered saline, polyols (e.g., glycerol, propylene glycol, liquid polyethylene glycol), dextrose solution and glycine. Intravenous vehicles can include various additives, preservatives, or fluid, nutrient or electrolyte replenishers (See, generally, Remington's Pharmaceutical Science, 16th Edition, Mack, Ed. 1980). The compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate. The compound can be lyophilized for storage and reconstituted in a suitable carrier prior to use according to art-known lyophilization and reconstitution techniques.

The optimum concentration of the active ingredient(s) in the chosen medium can be determined empirically, according to procedures known to the skilled artisan, and will depend on the ultimate pharmaceutical formulation desired.

The dosage ranges for the administration of the compound of the disclosure are those large enough to produce the desired effect. For example, the composition comprises a therapeutically or prophylactically effective amount of the compound.

As used herein, the term "effective amount" shall be taken to mean a sufficient quantity of the compound to inhibit/reduce/prevent signaling of VEGF-B in a subject. The skilled artisan will be aware that such an amount will vary depending on, for example, the compound and/or the particular subject and/or the type and/or the severity of stroke being treated. Accordingly, this term is not to be construed to limit the disclosure to a specific quantity, e.g., weight or number of compounds.

As used herein, the term "therapeutically effective amount" shall be taken to mean a sufficient quantity of compound to reduce or inhibit one or more symptoms of stroke.

As used herein, the term "prophylactically effective amount" shall be taken to mean a sufficient quantity of compound to prevent or inhibit or delay the onset of one or more detectable symptoms of stroke.

In one example, the compound is administered in an amount effective to have one or more of the following effects:

Reduce or prevent disruption of the blood brain barrier;
Reduce or prevent vascular permeability in the brain;
Reduce or prevent infarct size in the brain; and/or
Reduce or prevent intracranial hemorrhage.

The dosage should not be so large as to cause adverse side effects, such as hyper viscosity syndromes, pulmonary edema, congestive heart failure, and the like. Generally, the dosage will vary with the age, condition, sex and extent of the disease in the patient and can be determined by one of skill in the art. The dosage can be adjusted by the individual physician in the event of any complication.

Dosage can vary from about 0.1 mg/kg to about 300 mg/kg, e.g., from about 0.2 mg/kg to about 200 mg/kg, such as, from about 0.5 mg/kg to about 20 mg/kg, in one or more dose administrations daily, for one or several days.

In some examples, the compound is administered at an initial (or loading) dose which is higher than subsequent (maintenance doses). For example, the compound is administered at an initial dose of between about 1 mg/kg to about 30 mg/kg. The compound is then administered at a maintenance dose of between about 0.0001 mg/kg to about 1 mg/kg. The maintenance doses may be administered every 7-35 days, such as, every 14 or 21 or 28 days.

In some examples, a dose escalation regime is used, in which a compound is initially administered at a lower dose than used in subsequent doses. This dosage regime is useful in the case of subject's initially suffering adverse events In the case of a subject that is not adequately responding to treatment, multiple doses in a week may be administered. Alternatively, or in addition, increasing doses may be administered.

In one example, the compound(s) of the disclosure is used in combination with at least one additional known compound which is currently being used or is in development for preventing or treating stroke. Examples of such known compounds include but are not limited to common thrombolytic agents such as tissue plasminogen activators (e.g. alteplase, reteplase, tenecteplase), anistreplase, streptokinase, urokinase, lanoteplase, desmoteplase and staphylokinase.

Additionally, the methods of the disclosure may also include co-administration of at least one other therapeutic agent for the treatment of another disease directly or indirectly related to stroke, including but not limited to: dyslipidemia, hypertension, obesity, neuropathy, and/or retinopathy, etc. Additional examples of agents that can be co-administered with the compound(s) according to the invention are corticosteroids; immunosuppressive medications; antibiotics; antihypertensive and diuretic medications (such as ACE-inhibitors); lipid lowering agents such as bile sequestrant resins, cholestyramine, colestipol, nicotinic acid, and more particularly drugs and medications used to reduce cholesterol and triglycerides (e.g. fibrates (e.g. Gemfibrozil™) and HMG-CoA inhibitors such as Lovastatin™, Atorvastatin™, Fluvastatin™, Lescol™) Lipitor™, Mevacor™), Pravachol™, Pravastatin™, Simvastatin™, Zocor™, Cerivastatin™), etc); compounds that inhibit intestinal absorption of lipids (e.g. ezetiminde); nicotinic acid; and Vitamin D.

As will be apparent from the foregoing, the present disclosure provides methods of concomitant therapeutic treatment of a subject, comprising administering to a subject in need thereof an effective amount of a first compound and a second compound, wherein said agent is a compound of the disclosure (i.e., an inhibitor of VEGF-B signaling), and the second agent is for the prevention or treatment of stroke.

As used herein, the term "concomitant" as in the phrase "concomitant treatment" includes administering a first agent in the presence of a second agent. A concomitant therapeutic treatment method includes methods in which the first, second, third or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and as a second actor may administer to the subject a second agent and the administering steps may be executed at the same time, or nearly the same time, or at distant times, so long as the first agent (and/or additional agents) are after administration in the presence of the second agent (and/or additional agents). The actor and the subject may be the same entity (e.g. a human).

The time of administration of an additional therapeutic agent can be measured from the time of administration of the compound of the present invention. The interval can be, for example, 5 minutes to 24 or 48 hours. The interval may be for example, 15 min to 6 hours, 15 min to 4.5 hours, 15 min to 3 hours, 15 min to 1 hour, 30 minutes to 6 hours, or 30 min to 3 hours, or 30 min to 4.5 hours, or 1 to 3 hours, or 1 to 4.5 hours, or 1 to 5 hours, or 1 to 6 hours or 1 to 7 hours, or 1 to 8 hours, or 1 to 9 hours, or 1 to 10 hours.

In one example, the disclosure also provides a method for reducing an effect of stroke or for treating stroke in a subject, the method comprising administering to the subject a thrombolytic agent, wherein the subject is receiving or has previously received (e.g., since onset of a symptom of stroke) an inhibitor of VEGF-B signaling to a subject suffering from stroke and receiving another treatment.

Kits

Another example of the disclosure provides kits containing compounds useful for the treatment of stroke as described above.

In one example, the kit comprises (a) a container comprising a compound that inhibits VEGF-B signaling as described herein and/or a thrombolytic compound as described herein, optionally in a pharmaceutically acceptable carrier or diluent; and (b) a package insert with instructions for reducing an effect of stroke in a subject.

In accordance with this example of the disclosure, the package insert is on or associated with the container. Suitable containers include, for example, bottles, vials, syringes, etc. The containers may be formed from a variety of materials such as glass or plastic. The container holds or contains a composition that is effective for treating the stroke and may have a sterile access port (for example, the container may be an intravenous solution bag or a vial having a stopper pierceable by a hypodermic injection needle). At least one active agent in the composition is the compound that inhibits VEGF-B signaling. The label or package insert indicates that the composition is used for treating a subject eligible for treatment, e.g., one having or predisposed to stroke, with specific guidance regarding dosing amounts and intervals of compound and any other medicament being provided. The kit may further comprise an additional container comprising a pharmaceutically acceptable diluent buffer, such as bacteriostatic water for injection (BWFI), phosphate-buffered saline, Ringer's solution, and/or dextrose solution. The kit may further include other materials desirable from a commercial and user standpoint, including other buffers, diluents, filters, needles, and syringes.

The present disclosure includes the following non-limiting Examples.

EXAMPLES

Example 1

Increased Fatty Acid Uptake in Human Primary Brain derived Endothelial Cells In Vitro Reduced Glucose Uptake Primary Endothelial Cells Stimulated with VEGF-B have Increased Fatty Acid Uptake and Decreased Glucose Uptake Human primary brain micro-vascular endothelial cells, HBMECs, (passage number <5) were cultured in 24-well plates in endothelial basal medium with complement pack including 5% fetal bovine serum (FCS) in a cell culture incubator at 37° C., 5% $CO_2$. Six hours prior to stimulation, endothelial cells were starved by replacing FCS with fatty acid free bovine serum albumin (FAF-BSA). Cells were stimulated by addition of vehicle (Control), 100 ng/ml of VEGF-$B_{167}$ (B167), 100 ng/ml VEGF-$B_{186}$ (B186) or 2 µg/ml anti-VEGF-B antibody 2H10 for 2 hours.

After stimulation, uptake of BODIPY-labelled fatty acids (FA) or a fluorescent glucose analogue (2-NBDG) was measured. 2-NBDG was used as a marker of glucose uptake. Cells were incubated with BODIPY-C12 or 2-NBDG tracers for 5 or 20 minutes, respectively. Before adding the 2-NBDG, the cells were washed for 10 minutes with Kreb's Ringer buffer to remove culture media derived glucose. After incubation with FA or glucose tracers, cells were washed and fixed before image acquisition and quantification.

Stimulation with 100 ng/ml of either VEGF-B isoform (VEGF-$B_{167}$ or VEGF-$B_{186}$) significantly increased fatty acid (FA) uptake and significantly reduced glucose uptake. Treatment with the blocking VEGF-B antibody 2H10 alone did not significantly alter fatty acid or glucose uptake, yet a trend of decreased FA uptake and increased glucose uptake was observed indicative of endogenous production and secretion of VEGF-B in cultured endothelial cells.

These data show that cerebrovascular endothelial cells are able to respond to VEGF-B with increased FA uptake and decreased glucose uptake, suggesting that the uptake of lipids and glucose may be linked in a reciprocal manner in brain endothelium.

Figure 1B:
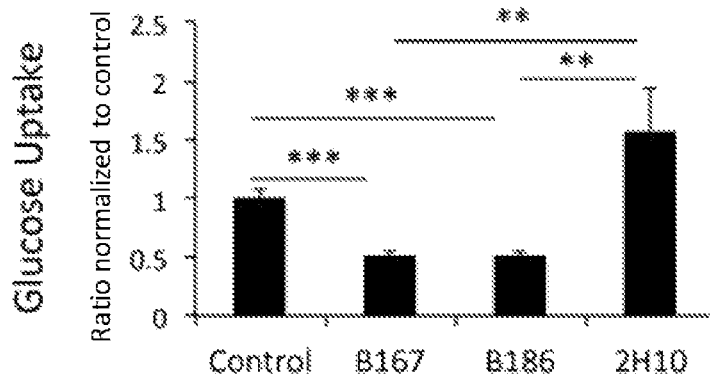
FIG. 1B is a graphical representation showing endothelial cell glucose uptake is significantly decreased after 2 hours treatment with VEGF-B proteins as measured using a fluorescent glucose analogue (2-NBDG). Values are ratio of uptake normalized to control. *P<0.05, P<0.01, *P<0.001 compared to control.

FIGS. 1A and 1B show increased FA uptake and decreased glucose uptake in primary brain derived endothelial cells treated with VEGF-B proteins.

Exposure of Primary Endothelial Cells to Fatty Acids Decreases Glucose Uptake

Human primary endothelial cells were grown in the presence or absence of a mixture of sodium palmitate and sodium oleate (50 µM) for 2 h or overnight and thereafter subjected to the 2-NBDG tracer and assayed for glucose uptake.

Endothelial cells exposed to a FA rich environment and lipid loading exhibit significantly decreased ability to take up glucose in vitro. This suggest that endothelial cells in a high lipid environment in vivo, such as in the diet-induced obesity (DIO) model, may respond similarly and that this would translate into decreased tissue glucose uptake in settings of DIO in vivo.

Figure 1C:
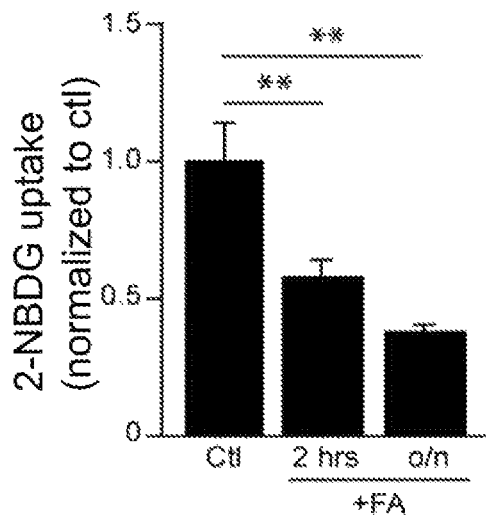
FIG. 1C is a graphical representation showing primary endothelial cells exposed to fatty acids (FA; 25 µM sodium palmitate and 25 µM sodium oleate) for 2 hours or overnight (o/n) show decreased ability to take up glucose (as measured using 2-NBDG). Values are means±SEM. **P<0.01 compared to controls.

FIG. 1C shows decreased glucose uptake in primary endothelial cells exposed to fatty acids. Endothelial cells exposed to lipid loading exhibit significantly decreased ability to take up glucose, suggesting that exposure and uptake of FA in endothelial cells decreases glucose uptake.

Example 2

Mice with Diet-induced Obesity have Increased Blood Glucose Levels and Increased Incidence of Ischemic Stroke Mice with Diet-induced Obesity (DIO) have Increased Blood Glucose Levels Three week old C57BL/6 mice were fed with high fat diet (60% calories from fat) or on a low fat control diet (normal chow, 10% calories from fat) for 15 weeks. Blood glucose was measured at the same time of the day after withdrawal of the food for 2 h as a mean to stabilize the blood glucose levels. The tip of the tail was cut and a drop of blood measured with a glucose meter.

DIO mice exhibited elevated blood glucose levels compared to age-matched mice on normal chow, in accordance with previous studies (Hagberg et al. Nature 2012; Collins et al. *Physiology & Behavior* 2004).

Figure 2A:
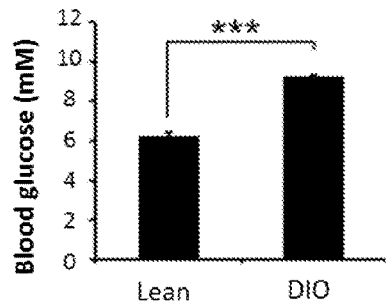
FIG. 2A is a graphical representation showing elevated blood glucose levels in diet-induced obese (DIO) mice compared with age-matched mice on normal chow. Values are means±SEM. ***P<0.001 compared to controls.

FIG. 2A shows that mice with DIO have increased blood glucose levels compared to age-matched mice on normal chow.

Mice with DIO have more Severe Strokes and Increased Incidence of Spontaneous Hemorrhage and Larger Infarcts Three week old male C57BL/6J mice were placed on a high fat diet (60% calories from fat) or on a low fat control diet (normal chow, 10% calories from fat), for a minimum of 12 weeks before inducing cerebral ischemia (middle cerebral artery occlusion (MCAO) model).

To induce cerebral ischemia using the MCAO model, mice were anesthetized with chloral hydrate (450 mg/kg) and placed securely under a dissecting microscope. The left MCA was exposed by craniotomy, and a laser Doppler flow probe placed on the surface of the cerebral cortex 1.5 mm dorsal median from the bifurcation of the MCA. The probe was connected to a flow meter and relative cerebral blood flow (CBF) determined from the tissue perfusion units (TPU) recorded with a continuous data acquisition program. A 3.5-mW 540 nm laser was directed at the MCA from a distance of 6 cm, and Rose Bengal dye (RB) (50 mg/kg), injected via the tail vein. Stable occlusion was achieved when the TPU drops to less than 20% of pre-occlusion levels and does not rebound within 10 min of laser withdrawal.

To determine infarct volumes, brains were removed, cut into 2-mm thick coronal sections and stained with 4% 2,3,5-triphenyltetrazolium-chloride (TTC). The areas of infarction at five coronal levels throughout the brain were identified and infarct and hemispheric volumes measured. Infarct volumes were calculated by measuring and subtracting the volume of the non-infarcted ipsilateral hemisphere from the volume of the contralateral hemisphere.

Mice with DIO had more severe strokes than lean mice, with a significantly increased incidence of spontaneous hemorrhage and larger infarcts. Stroke outcomes were significantly worse in the DIO model than in normal diet control mice, both in terms of infarct size, and an increased incidence of spontaneous intracerebral hemorrhages (ICH).

Figure 2B:
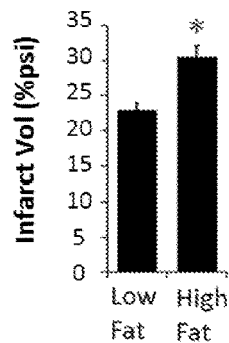
FIG. 2B is a graphical representation showing larger infarct volumes in DIO mice compared with age-matched mice on normal chow following ischemic stroke. Infarct volumes were measured at 72 h by TTC staining. Values are means±SEM, n=10 per group. *P<0.01 compared to controls.
Figure 2C:
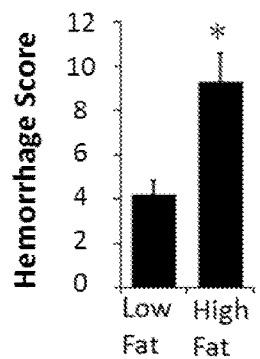
FIG. 2C is a graphical representation showing increased hemorrhage score in DIO mice compared with age-matched mice on normal chow following ischemic stroke. Hemorrhage was assessed at 72 h by a scoring system. Values are means ±SEM, n=10 per group. *P<0.01 compared to controls.

FIGS. 2B and 2C shows that mice with DIO have larger stroke volume and increased hemorrhage after ischemic stroke.

Mice with DIO have Significantly Increased Expression of the VEGF-B Receptor Nrp1 following Cerebral Ischemia DIO mice were subjected to MCAO, as described above. At 3 h post-ischemia, mice were perfused and sacrificed, and ipsi- and contralateral hemispheres homogenized and total RNA prepared. Transcript levels of Vegfb and its receptors Vegfr1 (Flt1) and Neuropilin-1 (Nrp1) were quantified by qPCR.

Neither Vegfb nor Vegfr1 expression was significantly increased by 3 h of ischemia, relative to the non-ischemic contralateral hemisphere, however expression of Nrp1 was increased nearly 3-fold in the ischemic hemisphere 3 h after MCAO, suggesting that VEGF-B signaling may increase locally during cerebral ischemia.

Figure 2D:
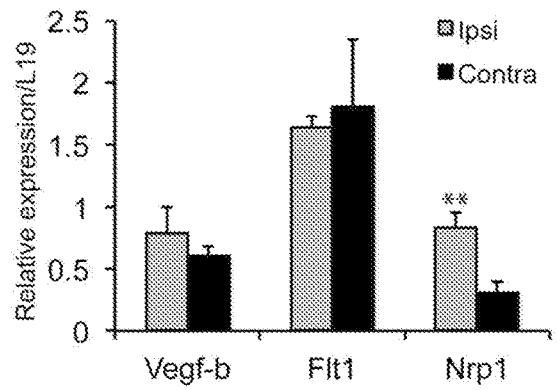
FIG. 2D is a graphical representation showing Nrp1 expression as measured by qPCR is increased in DIO mice 3 hours post ischemic stroke, whilst transcript levels of Vegfb and its receptor Vegfr1 (Flt1) were not significantly different to contralateral controls. Values are means±SEM, n=3 per group. **P<0.01 compared to controls.

FIG. 2D shows that Nrp1 expression, but not Vegf-b or Flt1 expression is significantly increased in mice with DIO following ischemic stroke.

Example 3

Prophylactic Treatment with a Neutralizing Anti-VEGF-B Antibody (2H10) Prevents Progression of Ischemic Stroke in Mice with DIO VEGF-B Antagonism Improves Glucose Uptake in Brains of Mice with DIO C57BL/6J mice were fed normal chow (lean) or a high fat chow (DIO) and DIO mice were treated with either isotype control or anti-VEGF-B 2H10 antibodies (16 mg/kg) twice a week for 30 weeks followed by [$^{18}$F]-DG PET imaging.

DIO reduced glucose uptake (as determined using the labelled glucose analogue) in the brain compared to lean control mice, and long-term inhibition of VEGF-B in mice with DIO significantly improved glucose uptake in the brain. These data suggest that similar to peripheral tissues, the systemic metabolic disturbances associated with DIO may reduce the ability of the brain to take up glucose from the blood, and that VEGF-B signaling may play a role in regulating CNS glucose metabolism in the DIO model.

Figure 3A:
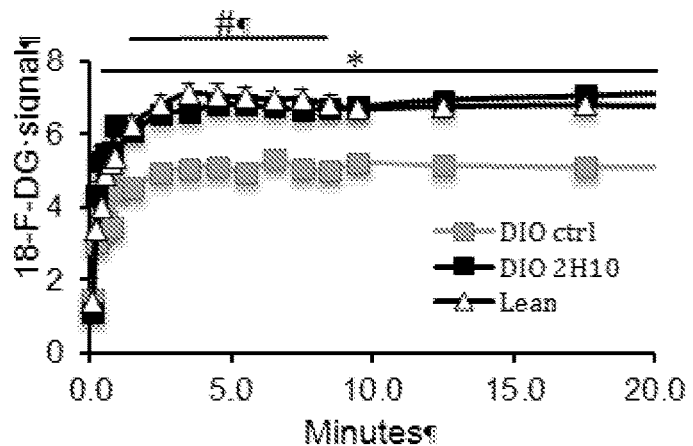
FIG. 3A is a graphical representation showing VEGF-B antagonism with 2H10 improves glucose analogue $^{18}$F-deoxyglucose (18FDG) uptake in the brains of DIO mice compared to mice treated with isotype control IgG. Glucose analogue uptake in 2H10 treated diet-induced obese mice was comparable to that observed in lean mice. n=2-5/group, Mean±SEM. #p<0.05, **p<0.01.

FIG. 3A shows VEGF-B antagonism with 2H10 improves glucose uptake in the brains of mice with DIO.

Prophylactic Anti-VEGF-B Treatment Significantly Reduces the Severity of Ischemic Stroke in Mice with DIO To directly test whether VEGF-B promotes neurovascular dysfunction and increases the severity of ischemic stroke in a background of metabolic disturbance, a thrombotic stroke was induced in mice with DIO, with and without treatment of the monoclonal antibody to VEGF-B, 2H10, or an isotype control.

Mice were treated for 1 week with 3 injections (I.P.) on days −7, −3, and 1 hour prior to MCAO with 16 mg/kg of either antibody. Mice were then subjected to photothrombotic MCAO and analyzed as described above. Treatment with a VEGF-B blocking antibody, 2H10, in a DIO background significantly reduces both infarct size and ICH.

Figure 3B:
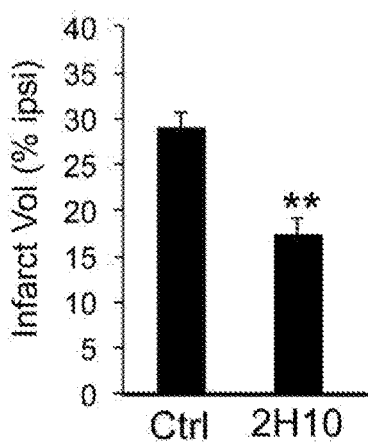
FIG. 3B is a graphical representation showing pre-treatment with the VEGF-B blocking antibody 2H10 decreases infarct volumes in DIO mice compared with age-matched mice on normal chow following ischemic stroke. Infarct volumes were measured at 72 h by 2,3,5-triphenyltetrazolium-chloride (TTC) staining. Values are means±SEM, n=10 per group. **P<0.01 compared to controls.
Figure 3C:
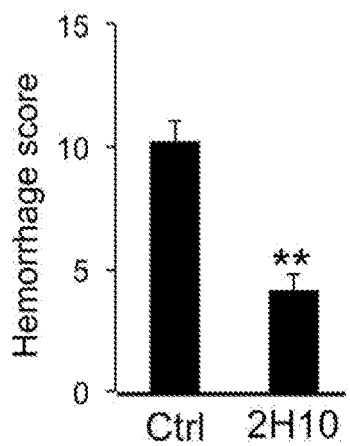
FIG. 3C is a graphical representation showing pre-treatment with the VEGF-B blocking antibody 2H10 decreases hemorrhage score in DIO mice compared with age-matched mice on normal chow following ischemic stroke. Hemorrhage was assessed at 72 h by a scoring system. Values are means±SEM, n=10 per group. **P<0.01 compared to controls.

FIGS. 3B and 3C shows prophylactic treatment with a VEGF-B blocking antibody (2H10) improves outcome after ischemic stroke in mice with DIO.

Mice with DIO Prophylactically Treated with Anti-VEGF-B Retain Expression of the Glucose Transporter Glut-1 following Cerebral Ischemia Three week old C57BL/6J mice were fed high fat chow for 17 weeks, after which they were pre-treated for 1 week, via IP injection on days −7, −3, and 1 hour prior to MCAO with 16 mg/kg of either isotype control or anti-VEGF-B 2H10 antibodies DIO mice pre-treated with control or 2H10 antibodies were perfused and fixed in PFA at 1 h post-MCAO and brains subjected to vibratome sectioning. Sections were stained with antibodies directed against Glut-1 and detected with immunofluorescence.

Staining for the glucose transporter Glut-1 in cerebral vessels of mice with DIO demonstrated that in the border of the ischemic zone, as early as 1 hour after MCAO, there was marked loss of Glut-1 staining compared to similar vessels in the non-ischemic hemisphere (contra).

One week pre-treatment with the VEGF-B blocking antibody 2H10 prior to MCAO partially preserved Glut-1 antigen in vessels of the penumbra. This suggests that blocking VEGF-B signaling with 2H10 may promote better glucose uptake by vessels in the ischemic penumbra by retaining Glut-1 glucose transporter function and that this in turn enables vessels in this region of diminished blood flow to better cope with the hypoxic and hypoglycemic environment of the penumbra.

Figure 3D:
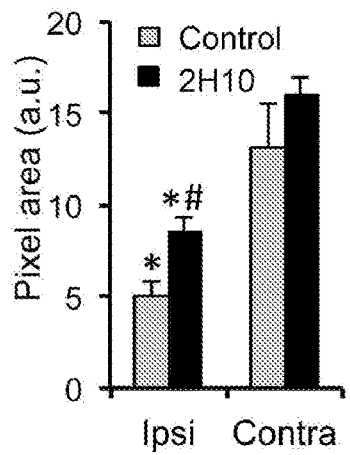
FIG. 3D is a graphical representation showing retained expression of the glucose transporter Glut-1 in the ischemic penumbra 1 hour after ischemic stroke following prophylactic treatment with the anti-VEGF-B antibody 2H10. N=5/group. Mean±SEM, *p<0.05 vs contra, #p<0.05 vs control.

FIG. 3D shows DIO mice pre-treated VEGF-B blocking antibody 2H10 correlated with retained plasma membrane expression of Glut-1 in the ischemic brain hemisphere compared with the non-ischemic contralateral hemisphere. Relative areas of immunofluorescence are plotted.

Prophylactic Anti-VEGF-B Treatment Reduces Blood-Brain-Barrier Leakage in Mice with DIO following Cerebral Ischemia DIO mice were pre-treated with 2H10 or isotype control antibodies as in above followed by MCAO. Immediately before induction of MCAO, mice were injected (IV) with a 70 kDa fluorescent dextran tracer to permit analysis of the BBB permeability. At 1 hour after MCAO induction, the mice were perfused and lightly post-fixated and brains analyzed for BBB permeability.

As early as 1 hour after MCAO a dramatic loss of BBB integrity was observed in mice with DIO. This was significantly reduced by treatment with the VEGF-B blocking antibody 2H10. This suggests that blocking VEGF-B improves cerebrovascular function in mice with DIO during the first hour of ischemia.

Figure 3E:
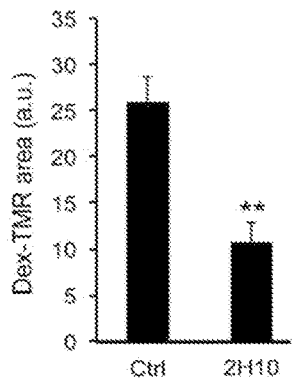
FIG. 3E is a graphical representation showing prophylactic treatment with the anti-VEGF-B antibody 2H10 in DIO mice reduces blood-brain-barrier leakage (as measured by Dextran extravasation) 1 hour after ischemic stroke. N=5/group, mean±SEM, ** p<0.01.

FIG. 3E shows pre-treatment with the VEGF-B blocking antibody 2H10 reduces blood-brain-barrier leakage 1 hour after ischemic stroke in mice with DIO.

Prophylactic Anti-VEGF-B Treatment Reduces Induction of Occludin Phosphorylation in Mice with DIO following Cerebral Ischemia DIO mice were pre-treated for one week with 2H10 or isotype control antibodies as above followed by MCAO. At 3 h post-ischemia, mice were perfused and brains collected and immediately frozen. Cryo-sections were obtained and subjected to immunofluorescent staining with a phosphoserine specific anti-Occludin antibody (serine residue 490) and fluorescence intensity quantified.

Occludin is a tight junction protein that is rapidly phosphorylated after MCAO and ischemia reperfusion injury (Muthusamy et al *Journal of cerebral blood flow and metabolism* 2014). It has previously been shown that phosphorylation of Occludin on Serine residue 490 is involved in BBB disruption and permeability (Murakami et al *Diabetes* 2012; Murakami et al *The Journal of Biological Chemistry* 2009).

Isotype control (IgG) treated DIO mice showed increased Occludin serine phosphorylation (pS490) in the penumbra (ipsi), compared to contralateral hemisphere (contra) 3 h after MCAO, indicating increased endothelial tight junction disassembly and vascular permeability in the ischemic hemisphere. Treatment with anti-VEGF-B antibody 2H10 diminished induction of Occludin phosphorylation in the ipsilateral hemisphere penumbra region supporting the notion that treatment with the anti-VEGF-B antibody 2H10 confers enhanced BBB integrity.

Figure 3F:
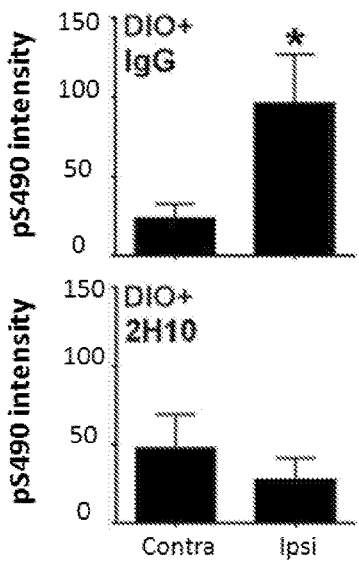
FIG. 3F is a graphical representation showing prophylactic anti-VEGF-B antibody treatment decreases Occludin serine phosphorylation (serine residue 490) following ischemic stroke in DIO mice compared to IgG control treated mice. Staining with a phosphoserine specific anti-Occludin antibody in the contralateral hemisphere and ipsilateral penumbra region were quantified and expressed as pixel intensity. N=3, *p<0.05.

FIG. 3F shows anti-VEGF-B treatment diminishes Occludin phosphorylation following ischemic stroke in mice with DIO.

Prophylactic Anti-VEGF-B Treatment Blocks Lipid Accumulation in Cerebral Blood Vessels in Mice with DIO following Cerebral Ischemia Since VEGF-B signaling down-regulates glucose uptake and increases lipid uptake (as shown above), cerebral vessels were examined for lipid accumulation after MCAO in lean and obese mice, and in obese mice treated with the 2H10 antibody.

DIO mice were pre-treated with 2H10 or isotype control antibodies as detailed above, followed by MCAO. DIO mice without pre-treatment and lean age-matched controls were also subjected to MCAO. At 3 h post-ischemia, mice were perfused and brains collected and immediately frozen. Cryosections were obtained, stained with an antibody to the lipid droplet coating protein, Adipophilin/Perilipin2 and quantified.

Within 3 h of MCAO significant uptake of lipids into cerebral vessels in the ischemic hemisphere was observed. Relative to the non-ischemic contralateral hemisphere, where very little adipophilin staining was observed, there was also significant uptake of lipids around vessel in the ischemic hemisphere of lean mice. However, this was significantly less than that seen in mice with DIO, and in these obese mice the increase in perivascular lipid accumulation was largely blocked by 2H10 treatment.

These data suggest that even in lean mice, MCAO rapidly induces lipid uptake, possibly to help meet metabolic demand in the ischemic tissue, and that DIO dramatically intensifies this response. Excessive and ectopic lipid accumulation in the cerebrovascular bed might however be harmful, especially in the context of oxygen and glucose deprivation after MCAO.

Figure 3G:
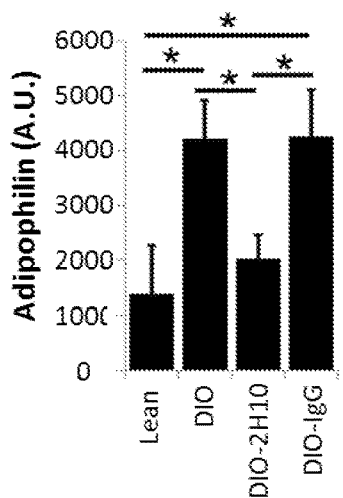
FIG. 3G is a graphical representation showing lipid accumulation (as measured by vascular adipophilin immunostaining) in cerebral blood vessels 3 h post ischemic stroke in DIO mice is blocked by prophylactic treatment with the anti-VEGF-B antibody 2H10 compared to isotype control treatment (IgG). Mean±SEM, **p<0.01.

FIG. 3G shows that lipid accumulation in cerebral blood vessels after ischemic stroke is blocked by prophylactic treatment with the anti-VEGF-B antibody 2H10.

Example 4

Therapeutic Anti-VEGF-B Treatment in Combination with tPA Thrombolysis Reduces Infarct Size, Hemorrhages and Increases Survival in Mice with DIO Mice with DIO were subjected to MCAO and treated 1 hr post stroke with 2H10 or isotype control antibodies (16 mg/kg), as detailed above. After an additional 4 hrs, the mice received thrombolytic therapy by intravenous infusion of tPA (Alteplase, 10 mg/kg) to dissolve the induced blood clots. Isolated brains of the surviving animals were then analyzed as described above.

Typically the efficacy of thrombolytic tPA treatment diminishes with time, while the risk of hemorrhagic conversion rises (Ahmed et al *Lancet Neurology* 2010). The present results show that 1 h delayed treatment with 2H10 after MCAO, followed by tPA thrombolysis 4 hrs later, reduced infarct size, reduces hemorrhages, and prevents lethal hemorrhages as the survival of the 2H10 treated animals was significantly higher compared to isotype treated controls that were subjected to late tPA thrombolysis.

The results suggest a therapeutic potential of VEGF-B antagonists in stroke as a potential adjuvant therapy to tPA treatment that may improve the safety of tPA thrombolysis by reducing hemorrhagic complications and/or may extend the treatment window for tPA. In a clinical setting, an extension of the therapeutic window is the most important step towards treatment of more patients with thrombolytic therapy.

Figures 4A, 4B:
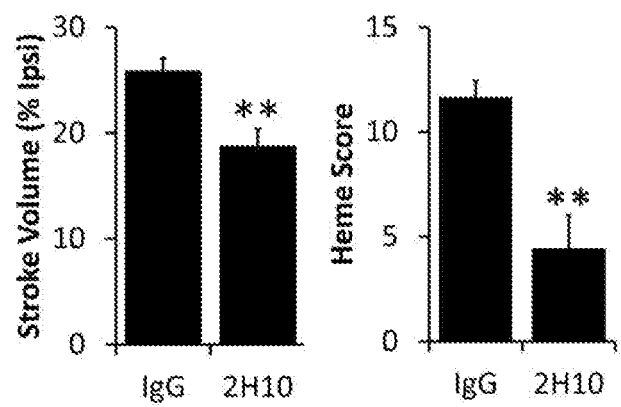
FIG. 4A is a graphical representation showing inhibition of VEGF-B with 2H10 antibody significantly reduces stroke volume after late thrombolysis in DIO mice following ischemic stroke. Infarct volumes were measure 72 hours after ischemic stroke by TTC staining. N=6-10/group, mean+SEM, **p<0.01.
FIG. 4B is a graphical representation showing inhibition of VEGF-B with 2H10 antibody significantly reduces hemorrhage score after late thrombolysis in DIO mice following ischemic stroke. Hemorrhage score was measured histologically 72 hours after ischemic stroke. N=6-10/group, mean+SEM, **p<0.01.
Figure 4C:
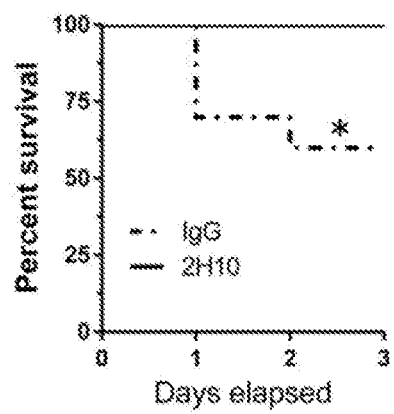
FIG. 4C is a Kaplan Meier survival analysis showing inhibition of VEGF-B with 2H10 antibodies improves survival outcomes after late thrombolysis in mice with diet-induced obesity following ischemic stroke. N=10/group, mean+SEM, *p<0.05.

FIGS. 4A-C shows inhibition of VEGF-B with the VEGF-B blocking antibody 2H10 improves outcomes after late thrombolysis.

The invention claimed is:

1. A method of reducing an effect of stroke in a subject, the method comprising administering to the subject a compound that inhibits VEGF-B signaling, wherein the compound that inhibits VEGF-B signaling is: an antibody or antigen binding fragment thereof that binds to or specifically binds to VEGF-B and neutralizes VEGF-B signaling, the antibody or antigen binding domain thereof comprising complementarity determining regions (CDRs) of a heavy chain variable region ($V_H$) comprising a sequence set forth in SEQ ID NO: 3, and CDRs of a light chain variable region ($V_L$), comprising a sequence set forth in SEQ ID NO: 4; and is administered after the stroke and in combination with a thrombolytic compound.

2. The method of claim 1, wherein the subject suffers from diabetes and/or obesity.

3. The method of claim 2, wherein the diabetes is type 2 diabetes.

4. The method of claim 1, wherein the subject has one or more of the following characteristics:
   (a) has already suffered from a stroke and/or a transient ischemic attack;
   (b) has a family history of stroke;
   (c) suffers from heart disease;
   (d) has high blood pressure;
   (e) has high plasma low density lipoprotein levels;
   (f) has metabolic syndrome
   (g) has a cardiac abnormality; and/or
   (h) has undergone cardiac surgery or hip replacement surgery.

5. The method of claim 1, wherein the compound that inhibits VEGF-B signaling is administered before the thrombolytic compound.

6. The method of claim 5, wherein administration of the compound that inhibits VEGF-B signaling extends the time in which the thrombolytic compound can safely be administered to the subject.

7. The method of claim 1, wherein the thrombolytic compound is administered more than two hours after onset of symptoms of a stroke.

8. The method of claim 1, wherein the subject has blood glucose levels greater than 400 mg/dL.

9. The method of claim 1, wherein the thrombolytic compound is selected from the group consisting of a tissue plasminogen activator, lanetoplase, reteplase, staphylokinase, streptokinase, anistreplase, desmoteplase or a urokinase.

10. The method of claim 1, wherein the compound that inhibits VEGF-B and/or the thrombolytic compound is administered in an amount sufficient to have one or more of the following effects:
    (a) reducing infarct size in the subject;
    (b) reducing the hemorrhage score as assessed by the intracerebral hemorrhage score in the subject;
    (c) reducing incidence of a hemorrhage in a subject;
    (d) reducing the likelihood of lethal hemorrhage in a subject;
    (e) reducing brain edema in the subject following stroke; and/or
    (f) reducing blood-brain-barrier breakdown or leakage in the subject following stroke.

11. The method of claim 1, wherein the stroke is an ischemic stroke.

12. The method of claim 1, wherein the compound that inhibits VEGF-B signaling comprises an Fv.

13. The method of claim 12, wherein the compound that inhibits VEGF-B signaling is selected from the group consisting of:
    (i) a single chain Fv fragment (scFv);
    (ii) a dimeric scFv (di-scFv);
    (iii) a diabody;
    (iv) a triabody;
    (v) a tetrabody;
    (vi) a Fab;
    (vii) a F(ab')$_2$;

(viii) one of (i) to (vii) linked to a constant region of an antibody, Fc or a heavy chain constant domain ($C_H$)2 and/or $C_H$3; and
(ix) an antibody.

14. The method of claim 13, wherein the antibody:
(i) comprises a humanized variable region of the $V_H$ comprising a sequence set forth in SEQ ID NO: 3 and $V_L$ comprising a sequence set forth in SEQ ID NO: 4; or
(ii) comprises a $V_H$ comprising a sequence set forth in SEQ ID NO: 5 and a $V_L$ comprising a sequence set forth in SEQ ID NO:6.

15. The method of claim 1, wherein the compound that inhibits VEGF-B signaling is an antibody or antigen binding fragment thereof comprising:
(i) a $V_H$ comprising:
  (a) a CDR1 comprising a sequence set forth in SEQ ID NO: 21;
  (b) a CDR2 comprising a sequence set forth in SEQ ID NO: 22; and
  (c) a CDR3 comprising a sequence set forth in SEQ ID NO: 23; and
(ii) a $V_L$ comprising:
  (a) a CDR1 comprising a sequence set forth in SEQ ID NO: 18;
  (b) a CDR2 comprising a sequence set forth in SEQ ID NO: 19; and
  (c) a CDR3 comprising a sequence set forth in SEQ ID NO: 20.

16. The method of claim 1, wherein the thrombolytic compound is administered between two and six hours after onset of symptoms of a stroke.

* * * * *